(12) United States Patent
Jäkel et al.

(10) Patent No.: US 7,696,349 B2
(45) Date of Patent: Apr. 13, 2010

(54) METHOD FOR ASYMMETRIC SYNTHESIS

(75) Inventors: Christoph Jäkel, Limburgerhof (DE);
Martin Volland, Heidelberg (DE);
Thomas Mackewitz, Römerberg (DE);
Rocco Paciello, Bad Dürkheim (DE);
Bernhard Breit, Gundelfingen (DE);
Wolfgang Seiche, Heidelberg (DE);
Martine Weis, Freiburg (DE);
Christoph Waloch, Freiburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/237,154

(22) Filed: Sep. 24, 2008

(65) Prior Publication Data

US 2009/0326226 A1    Dec. 31, 2009

Related U.S. Application Data

(63) Continuation of application No. 10/580,322, filed as application No. PCT/EP2004/013344 on Nov. 24, 2004, now Pat. No. 7,442,842.

(30) Foreign Application Priority Data

Nov. 25, 2003   (DE) .................. 103 55 066

(51) Int. Cl.
*C07F 9/80* (2006.01)
(52) U.S. Cl. ........................................... 546/3
(58) Field of Classification Search ............ 546/3
See application file for complete search history.

(56) References Cited

U.S. PATENT DOCUMENTS

| 4,687,874 | A | 8/1987 | Oswald et al. |
| 4,786,443 | A | 11/1988 | Drent et al. |
| 4,940,787 | A | 7/1990 | Drent |
| 6,399,834 | B1 | 6/2002 | Leitner et al. |
| 2004/0199024 | A1 | 10/2004 | Mackewitz et al. |

FOREIGN PATENT DOCUMENTS

| EP | 0 684 249 A1 | 3/1994 |
| EP | 0 614 870 A2 | 9/1994 |
| EP | 0 614 901 A1 | 9/1994 |
| EP | 0 614 902 A1 | 9/1994 |
| EP | 0 614 903 A2 | 9/1994 |
| WO | WO-80/01690 A1 | 8/1980 |
| WO | WO-93/03839 A1 | 3/1993 |

OTHER PUBLICATIONS

"Chemistry of Heterocyclic Compounds. 27. An Improved Preparation of Pyridyldiphenylphosphines", George R. Newkome et al., *J. Org. Chem.*, vol. 43, No. 5, 1978 pp. 947-949.

"Synthesis, Solid-State Structures, and Aggregation Motifs of Phosphines and Phosphine Oxides Bearing One 2-Pyridone Ring", by Motohiro Akazome et al., *J. Org. Chem.* 2000, vol. 65, No. 21, pp. 6917-6921.

"Hydrogen Bonding as a Construction Element for Bidentate Donor Ligands in Homogeneous Catalysis: Regioselective Hydroformylation of Terminal Alkenes" by Bernhard Breit et al., *J. Am. Chem. Soc.* vol. 125, No. 22, 2003 pp. 6608-6609.

"Homogeneous catalysis with transition metal complexes" vol. 79, Chapter 6 pp. 199-248 *Studies in Surface Science and Catalysis* 1993.

"Rhodium-Catalysed Asymmetric Hydroformylation of Unsaturated Nitriles" by Marielle M.H. Lambers-Verstappen et al., *Adv. Synth. Catal.* 2003, 345, No. 4 pp. 478-482.

*Primary Examiner*—Taofiq A Solola
(74) *Attorney, Agent, or Firm*—Connolly Bove Lodge & Hutz LLP

(57) ABSTRACT

The present invention relates to a process for asymmetric synthesis in the presence of a chiral catalyst comprising at least one complex of a metal of transition group VIII with ligands capable of dimerization via noncovalent bonds, such catalysts and their use.

4 Claims, 1 Drawing Sheet

METHOD FOR ASYMMETRIC SYNTHESIS

The present invention relates to a process for asymmetric synthesis in the presence of a chiral catalyst comprising at least one complex of a metal of transition group VIII with ligands capable of dimerization via noncovalent bonds, such ligands and catalysts and their use.

The term asymmetric synthesis refers to reactions in which a chiral group is generated from a prochiral group such that the stereoisomeric products (enantiomers or diastereomers) are formed in unequal amounts. Asymmetric synthesis has acquired tremendous importance especially in the pharmaceutical industry, since it is frequently the case that only a particular optically active isomer is therapeutically active. There is thus a continuing need for new methods of carrying out asymmetric syntheses and specific catalysts having a high degree of asymmetric induction for particular stereocenters, i.e. the synthesis should lead to the desired isomer in high optical purity and in high chemical yield.

An important class of reactions is addition onto carbon-carbon and carbon-heteroatom multiple bonds. Addition onto the two adjacent atoms of a C=X double bond (X=C, heteroatom) is also referred to as 1,2-addition. Addition reactions can also be characterized according to the groups added on, with hydroaddition being the addition of a hydrogen atom and carboaddition being the addition of a carbon-comprising fragment. Thus, a 1-hydro-2-carboaddition is the addition of hydrogen and a carbon-comprising group. Important representatives of this reaction are, for example, hydroformylation, hydrocyanation and carbonylation. A further very important addition onto carbon-carbon and carbon-heteroatom multiple bonds is hydrogenation. There is a need for catalysts for asymmetric addition reactions of prochiral ethylenically unsaturated compounds that have good catalytic activity and high stereoselectivity.

Hydroformylation or the oxo process is an important industrial process and is employed for preparing aldehydes from olefins, carbon monoxide and hydrogen. These aldehydes can, if appropriate. be hydrogenated by means of hydrogen in the same process to give the corresponding oxo alcohols. Asymmetric hydroformylation is an important method for synthesizing chiral aldehydes and is of interest as a route to chiral building blocks for the preparation of flavors, cosmetics, crop protection agents and pharmaceuticals. The hydroformylation reaction itself is strongly exothermic and generally proceeds under superatmospheric pressure and at elevated temperatures in the presence of catalysts. Catalysts used are Co, Rh, Ir, Ru, Pd or Pt compounds or complexes which may be modified with N-, P-, As- or Sb-comprising ligands to influence the activity and/or selectivity. In the hydroformylation reaction of olefins having more than two carbon atoms, the formation of mixtures of isomeric aldehydes can occur due to the possible addition of CO onto each of the two carbon atoms of a double bond. In addition, double bond isomerization can result in the formation of mixtures of isomeric olefins and possibly also isomeric aldehydes when using olefins having at least four carbon atoms. To achieve efficient asymmetric hydroformylation, the following conditions therefore have to be met:

1. high activity of the catalyst, 2. high selectivity in respect of the desired aldehyde and 3. high stereoselectivity in favor of the desired isomer.

The use of phosphorus-comprising ligands for stabilizing and/or activating the catalyst metal in rhodium-catalyzed low-pressure hydroformylation is known. Suitable phosphorus-comprising ligands are, for example. phosphines, phosphinites, phosphonites, phosphites, phosphoramidites, phospholes and phosphabenzenes. The most widespread ligands at present are triarylphosphines, e.g. triphenylphosphine and sulfonated triphenylphosphine, since these have sufficient stability under the reaction conditions.

It is known that the use of chelating ligands which have two groups capable of coordination has an advantageous effect on the stereoselectivity achieved in asymmetric hydroformylation reactions. Thus, for example, M. M. H. Lambers-Verstappen and J. de Vries describe the rhodium-catalyzed hydroformylation of unsaturated nitriles in Adv. Synth. Catal. 2003, 345, No. 4, pp. 478-482, but were able to achieve a satisfactory asymmetric hydroformylation only when using asymmetric BINAPHOS ligands. Furthermore, it is known that the use of chelating ligands also has an advantageous effect on the n-selectivity achieved in hydroformylation (cf. Moulijn, van Leeuwen and van Santen, Catalysis, vol. 79, pp. 199-248, Elsevier 1993). However, a disadvantage of the use of chelating ligands is that complicated syntheses are frequently required for their preparation and/or they are obtained only in poor yields.

In J. Org. Chem. 2000, 65, pp. 6917-6921, M. Akazome et al. describe the synthesis, solid state structure and aggregation behavior of phosphines which bear a 2-pyridone ring. In J. Org. Chem. 1978, 43, pp. 947-949, G. R. Newkome and D. C. Hager describe a process for preparing pyridyldiphenylphosphines. Use as ligands in transition metal catalysts is not described in these documents. U.S. Pat. No. 4,786,443 and U.S. Pat. No. 4,940,787 describe processes for the carbonylation of acetylenically unsaturated compounds in the presence of a palladium catalyst. Ligands used are phosphines which bear at least one hetaryl radical, e.g. an optionally substituted pyridyl radical. The use of phosphines which have at least one group capable of forming noncovalent bonds as ligands is not described.

WO 80/01690 describes a rhodium catalyst comprising at least one phosphine ligand in which two aryl groups and, via an alkylene bridge, a heteroatom-comprising radical are bound to the P atom. This heteroatom-comprising radical can be one of a large number of different radicals, with radicals comprising carboxamide groups being mentioned among others. However, this document does not teach the use of ligands having a functional group which is capable of forming intermolecular noncovalent bonds. Thus, the only working example involving ligands comprising carboxamide groups concerns (N-2-pyrrolidinonylethyl)diphenylphosphine, which is not capable of forming intermolecular noncovalent bonds between the amide groups. U.S. Pat. No. 4,687,874 has a disclosure content comparable to WO 80/01690.

The unpublished German patent application P 10313319.4 describes a hydroformylation process which is suitable for the hydroformylation of 1-olefins with high n-selectivity. It uses hydroformylation catalysts based on monophosphorus ligands which are capable of forming intermolecular noncovalent bonds. Such ligands can in principle dimerize via intermolecular noncovalent bonds and thus form pseudochelate complexes.

In J. Am. Chem. Soc. 2003, 125, 6608-6609, B. Breit and W. Seiche describe the dimerization of monodentate ligands via hydrogen bonds to form bidentate donor ligands and their use in hydroformylation catalysts having a high regioselectivity.

None of the abovementioned documents is concerned with chiral ligands or catalysts for use in asymmetric syntheses.

EP-A-0 614 870 describes a process for preparing optically active aldehydes by hydroformylation of prochiral 1-olefins in the presence of a rhodium complex comprising an unsymmetrical phosphorus-comprising ligand having a 1,1'-binaphthylene backbone as hydroformylation catalyst. The synthesis of the unsymmetrical phosphorus-comprising ligands is complicated. EP-A-0 614 901, EP-A-0 614 902, EP-A-0 614 903, EP-A-0 684 249 and DE-A-198 53 748 describe unsymmetrical phosphorus-comprising ligands having a comparable structure.

WO 93/03839 (EP-B-0 600 020) describes an optically active metal-ligand catalyst complex comprising an optically active pnicogen compound as ligand and processes for asymmetric synthesis in the presence of such a catalyst.

It is an object of the present invention to provide a process for preparing chiral compounds with high stereoselectivity. In addition, the desired isomer should also be obtained in high yield. A specific object of the invention is to provide a process which is suitable for the hydrogenation of carbon-carbon and carbon-heteroatom multiple bonds with high stereoselectivity. A further specific object of the present invention is to provide a hydroformylation process which is suitable for the hydroformylation of olefins with high stereoselectivity. The processes should preferably use catalysts whose ligands can be prepared easily and in good yields.

It has now surprisingly been found that this object is achieved by the provision of chiral catalysts based on monopnicogen ligands or monopseudopnicogen ligands which are capable of forming intermolecular noncovalent bonds. Such ligands can in principle dimerize via intermolecular noncovalent bonds and thus form pseudochelate complexes.

The present invention accordingly provides a process for preparing chiral compounds by reacting a prochiral compound comprising at least one ethylenically unsaturated double bond with a substrate in the presence of a chiral catalyst comprising at least one transition metal complex with ligands which each have a pnicogen-comprising or pseudopnicogen-comprising group and at least one functional group capable of forming intermolecular, noncovalent bonds, with the complex comprising ligands dimerized via intermolecular noncovalent bonds.

Figure 1:
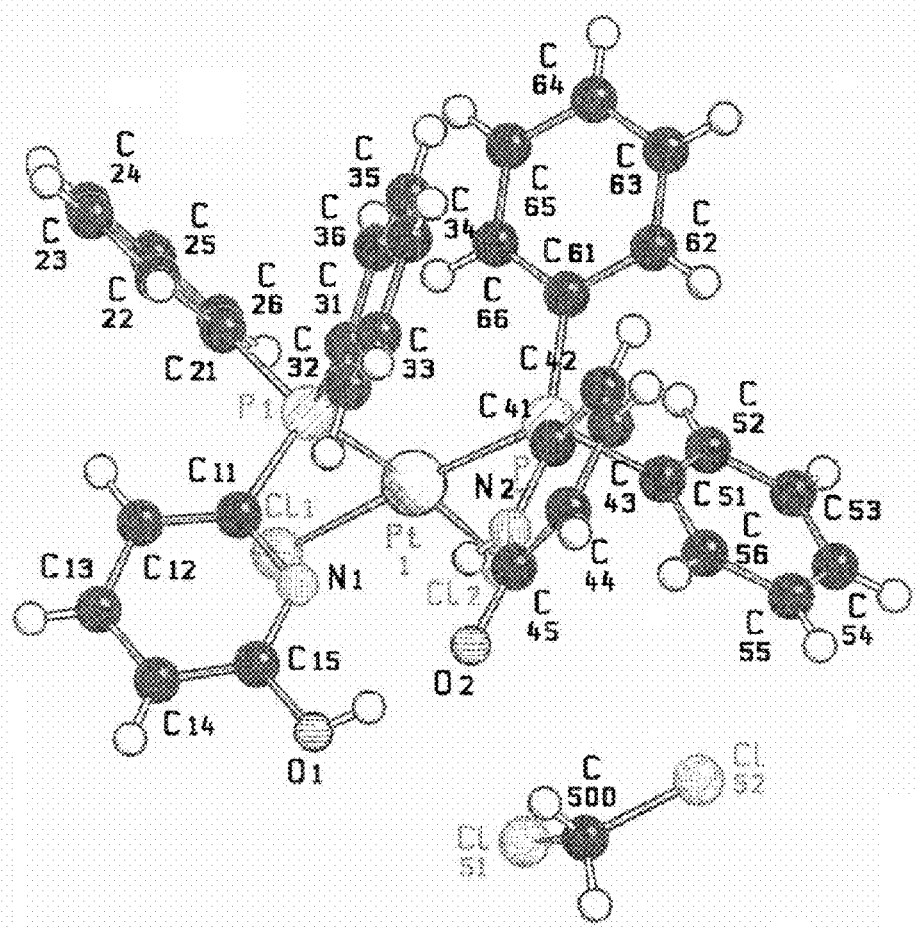
FIG. 1 depicts a dimeric platinum complex with 6-(diphenylphosphino)pyridin-2-ol and its tautomer.

In addition, the present invention provides ligands which each have one pnicogen-comprising or pseudopnicogen-comprising group and at least one functional group capable of forming intermolecular, noncovalent bonds, and also chiral catalysts.

The term "pnicogen atom" refers to an atom of main group V of the Periodic Table of the Elements. Preferred pnicogen atoms are N, P, As and Sb, with particular preference being given to N and P. If the pnicogen atom is a nitrogen atom, this is preferably present as an imine (=N—), i.e. it has a double bond to an adjacent atom. In particular, a P atom is used as pnicogen atom.

The term "pseudopnicogen atom" refers to an atom which behaves in the same way as a pnicogen atom. A preferred pseudopnicogen atom is the carbene carbon atom. Correspondingly, a "pseudopnicogen-comprising group" is a group which behaves the same as a pnicogen-comprising group. Preferred pseudopnicogen-comprising groups are N-heterocyclic carbenes as are described by W. A. Herrmann in Angew. Chem. 2002, 114, pp. 1342-1363. The disclosure of this document is hereby fully incorporated by reference.

For the purposes of the present invention, "chiral compounds" are compounds having at least one center of chirality (i.e. at least one asymmetric atom, in particular at least one asymmetric C atom or P atom), an axis of chirality, a plane of chirality or a helical structure.

For the purposes of the present invention, the term "chiral catalyst" is interpreted broadly. It comprises both catalysts having at least one chiral ligand and catalysts which have intrinsically achiral ligands but display center chirality, axial chirality, planar chirality or helicity due to the arrangement of the ligands as a result of noncovalent interactions and/or the arrangement of the ligands in complexed form.

"Achiral compounds" are compounds which are not chiral.

For the purposes of the present invention, a "prochiral compound" is a compound having at least one prochiral center. "Asymmetric synthesis" refers to a reaction in which a compound having at least one center of chirality, an axis of chirality, a plane of chirality or a helical structure is produced from a compound having at least one prochiral center, with the stereoisomeric products being formed in unequal amounts.

"Stereoisomers" are compounds having the same constitution but a different arrangement of atoms in three-dimensional space.

"Enantiomers" are stereoisomers which are mirror images of one another. The "enantiomeric excess" (ee) achieved in an asymmetric synthesis is given by the formula: ee[%]=(R−S)/(R+S)×100. R and S are the descriptors of the CIP system for the two enantiomers and indicate the absolute configuration around an asymmetric atom. The enantiomerically pure compound (ee=100%) is also referred to as a "homochiral compound".

The process of the invention leads to products which are enriched in a particular stereoisomer. The "enantiomeric excess" (ee) achieved is generally at least 20%, preferably at least 50%, in particular at least 80%.

"Diastereomers" are stereoisomers which are not enantiomers of one another.

It has surprisingly been found that chiral catalysts which comprise at least one complex with monopnicogen ligands or monopseudopnicogen ligands (ligands which have only one pnicogen-comprising group or pseudopnicogen-comprising group per molecule) and are capable of forming, via intermolecular noncovalent bonds, dimers in which the distance between the two pnicogen atoms/pseudopnicogen atoms is in a range usual for chelating ligands achieve a stereoselectivity in asymmetric synthesis which is as high as that which is otherwise achieved only when using chelating ligands. In addition, the regioselectivity typical of chelating ligands can generally also be achieved when using these catalysts. Thus, for example, when they are used in hydroformylation, they can achieve n-selectivities of a level which is otherwise achieved only when using chelating ligands.

Ligands which are capable of forming dimers via intermolecular, noncovalent bonds are also referred to as pseudochelating ligands for the purposes of the present invention.

According to the invention, ligands which have a functional group capable of forming intermolecular, noncovalent bonds are used. These bonds are preferably hydrogen bonds or ionic bonds, in particular hydrogen bonds. In a preferred embodiment, the functional groups can be groups capable of tautomerism. The functional groups capable of forming intermolecular noncovalent bonds make the ligands capable of association, i.e. formation of aggregates in the form of dimers.

For the purposes of the present invention, a pair of functional groups of two ligands which are capable of forming intermolecular noncovalent bonds are referred to as "complementary functional groups". "Complementary compounds"

are ligand/ligand pairs which have functional groups which are complementary to one another. Such pairs are capable of association, i.e. formation of aggregates.

The functional groups capable of forming intermolecular noncovalent bonds are preferably selected from among hydroxyl, primary, secondary and tertiary amino, thiol, keto thioketone, imine, carboxylic ester, carboxamide, amidine, urethane, urea, sulfoxide, sulfoximine, sulfonamide and sulfonic ester groups.

These functional groups are preferably self-complementary functional groups, i.e. the formation of the noncovalent bonds occurs between two identical functional groups of the ligands used. Functional groups capable of tautomerism can each be present in the dimers in the form of identical or different isomers (tautomers). For instance, in the case of keto-enol tautomerism, both mono(pseudo)pnicogen ligands can be in the keto form, both can be in the enol form or one can be in the keto form and the other in the enol form. Of course, the ligand/ligand pairs can also be formed by two different ligands.

The distance between the atoms of the pnicogen-comprising or pseudopnicogen-comprising groups of the dimerized ligands which coordinate to the transition metal is preferably not more than 5 Å. It is preferably in a range from 2.5 to 4.5 Å, particularly preferably from 3.5 to 4.2 Å.

Suitable methods of determining whether the ligands used are capable of forming dimers include crystal structure analysis, nuclear magnetic resonance spectroscopy and molecular modeling. The ligands in uncomplexed form can generally be employed for the determination. This applies in particular to molecular modeling methods. In addition, it has been found that crystal structure analysis carried out on the solid, nuclear magnetic resonance spectroscopy in solution and calculation of the structure for the gas phase all generally provide reliable predictions regarding the behavior of the ligands used under the reaction conditions of the reaction being catalyzed. Thus, for example, ligands which according to the abovementioned methods of determination are capable of forming dimers generally also display properties as are otherwise usual only for chelating ligands under the conditions of the reactions in which they are used. Such properties include, in particular, achievement of a high stereoselectivity in the hydrogenation and hydroformylation of prochiral olefins. Furthermore, it has been found that this high stereoselectivity is no longer achieved when the formation of intermolecular noncovalent bonds between the ligands is disrupted in the reaction by addition of acids or protic solvents such as methanol.

In a suitable method of determining whether a ligand is suitable for the process of the invention, all possible hydrogen-bonded dimers of the ligand and its tautomers are firstly produced by means of a graphical molecular modeling program. These dimer structures are then optimized by means of quantum-chemical methods. This is preferably done using density functional theory (DFT), for example using Functional B-P86 (A. D. Becke, Phys. Rev. A 1988, 38, 3098; J. P. Perdew, Phys. Rev. B 1986, 33, 8822; ibid 1986, 34, 7406(E)) and Basis SV(P) (A. Schäfer, H. Horn, R. Ahlrichs, J. Chem. Phys. 1992, 97, 2571) in the program package Turbomole (R. Ahlrichs, M. Bacr, M. Haser, H. Horn, C. Kolmel, Chem. Phys. Lett. 1989, 162, 165; M. v. Arnim, R. Ahlrichs; J. Comput. Chem. 1998, 19, 1746) (obtainable from the University of Karlsruhe). A suitable commercially available molecular modeling package is Gaussian 98 (M. J. Frisch, J. A. Pople et al., Gaussian 98, Revision A.5, Gaussian Inc., Pittsburgh (Pa.) 1998).

Preferred pseudochelating ligands are ones in which the distance between the coordinating atoms. e.g. the P atoms, in the calculated dimer structure is less than 5 Å.

For the purposes of the description of the present invention, the expression "alkyl" comprises straight-chain and branched alkyl groups. These are preferably straight-chain or branched $C_1$-$C_{20}$-alkyl groups, more preferably $C_1$-$C_{12}$-alkyl groups, particularly preferably $C_1$-$C_8$-alkyl groups and very particularly preferably $C_1$-$C_4$-alkyl groups. Examples of alkyl groups are, in particular, methyl, ethyl, propyl, isopropyl, n-butyl. 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also comprises substituted alkyl groups which generally have 1, 2, 3, 4 or 5 substituents, preferably 1, 2 or 3 substituents and particularly preferably 1 substituent. These are preferably selected from among alkoxy, cycloalkyl, aryl, hetaryl, hydroxyl, halogen, $NE^1E^2$, $NE^1E^2E^{3+}$, carboxylate and sulfonate. A preferred perfluoroalkyl group is trifluoromethyl.

For the purposes of the present invention, the expression "alkylene" refers to straight-chain or branched alkanediyl groups having from 1 to 5 carbon atoms.

For the purposes of the present invention, the expression "cycloalkyl" comprises unsubstituted and substituted cycloalkyl groups, preferably $C_5$-$C_7$-cycloalkyl groups such as cyclopentyl, cyclohexyl or cycloheptyl. If they are substituted, these can generally bear 1, 2, 3, 4 or 5 substituents, preferably 1, 2 or 3 substituents and particularly preferably 1 substituent. These substituents are preferably selected from among alkyl, alkoxy, $NE^1E^2$, $NE^1E^2E^{3+}$ and halogen.

For the purposes of the present invention, the expression "heterocycloalkyl" comprises saturated, cycloaliphatic groups which generally have from 4 to 7, preferably 5 or 6, ring atoms and in which 1 or 2 of the ring carbons are replaced by heteroatoms selected from among the elements oxygen, nitrogen and sulfur and which may be substituted. If they are substituted, these heterocycloaliphatic groups can bear 1, 2 or 3 substituents, preferably 1 or 2 substituents, particularly preferably 1 substituent. These substituents are preferably selected from among alkyl, alkoxy, aryl, $COOR^o$, $COO^-M^+$, hydroxyl, halogen and $NE^1E^2$, with particular preference being given to alkyl radicals. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl. thiazolidinyl, isothiazolidinyl, isoxazolidinyl, piperazinyl. tetrahydrothienyl, tetrahydrofuranyl, tetrahydropyranyl, dioxanyl.

For the purposes of the present invention, the expression "aryl" comprises unsubstituted and substituted aryl groups and preferably refers to phenyl, tolyl, xylyl, mesityl, naphthyl, fluorenyl, anthracenyl, phenanthrenyl or naphthacenyl, particularly preferably phenyl or naphthyl. If they are substituted, these aryl groups can generally bear 1, 2, 3, 4 or 5 substituents, preferably 1, 2 or 3 substituents and particularly preferably 1 substituent, selected from among the groups alkyl, alkoxy, carboxylate. trifluoromethyl, sulfonate, $NE^1E^2$, alkylene-$NE^1E^2$, nitro, cyano and halogen. A preferred perfluoroaryl group is pentafluorophenyl.

For the purposes of the present invention, the expression "hetaryl" comprises unsubstituted or substituted, heterocycloaromatic groups, preferably the groups furyl, thienyl, pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl. 1,2,3-triazolyl, 1,3,4-triazolyl and carbazolyl. If they are substituted, these heterocycloaromatic groups can generally bear 1, 2 or 3 substituents selected from among the groups alkyl, alkoxy, hydroxyl, carboxylate, sulfonate $NE^1E^2$, alkylen-$NE^1E^2$ and halogen.

For the purposes of the present invention, carboxylate and sulfonate are preferably derivatives of a carboxylic acid function or a sulfonic acid function, in particular a metal carboxylate or sulfonate, a carboxylic ester or sulfonic ester function or a carboxamide or sulfonamide function. Such derivatives include, for example, the esters with $C_1$-$C_4$-alkanols such as methanol, ethanol, n-propanol, isopropanol, n-butanol, sec-butanol and tert-butanol.

What has been said above with regard to the expressions "alkyl", "cycloalkyl", "aryl", "heterocycloalkyl" and "hetaryl" applies analogously to the expressions "alkoxy", "cycloalkoxy", "aryloxy", "heterocycloalkoxy" and "hetaryloxy".

For the purposes of the present invention, the expression "acyl" refers to alkanoyl or aroyl groups generally having from 2 to 11, preferably from 2 to 8, carbon atoms, for example the formyl, acetyl, propanoyl, butanoyl, pentanoyl, hexanoyl, heptanoyl-, 2-ethylhexanoyl, 2-propylheptanoyl, benzoyl or naphthoyl group.

The radicals $E^1$ to $E^{12}$ are selected independently from among hydrogen, alkyl, cycloalkyl and aryl. The groups $NE^1E^2$, $NE^4E^5$, $NE^7E^8$ and $NE^{10}DE^{11}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

$M^+$ is a cation equivalent, i.e. a monovalent cation or the part of a polyvalent cation corresponding to a single positive charge. The cation $M^+$ serves merely as counterion to neutralize negatively charged substituent groups such as the $COO^-$ or sulfonate group and can in principle be selected freely. Preference is therefore given to using alkali metal ions, in particular $Na^+$, $K^+$, $Li^+$ ions, or onium ions, such as ammonium, monoalkylammonium, dialkylammonium, trialkylammonium, tetraalkylammonium, phosphonium, tetraalkylphosphonium or tetraarylphosphonium ions.

An analogous situation applies to the anion equivalent $X^!$ which serves merely as counterion of positively charged substituent groups such as ammonium groups and can be selected freely from among monovalent anions and the parts of a polyvalent anion corresponding to a single negative charge. Preference is generally given to halide ions $X^-$, in particular chloride and bromide.

x and y are each an integer from 1 to 240, preferably an integer from 2 to 120.

For the purposes of the present invention, the term "polycyclic compound" comprises in the broadest sense compounds which comprise at least two rings, regardless of the way in which these rings are linked. The rings can be carbocyclic and/or heterocyclic. The rings can be linked via single or double bonds ("multinuclear compounds"), be joined by fusion ("fused ring systems") or be bridged ("bridged ring systems", "cage compounds"). Preferred polycyclic compounds are fused ring systems.

Fused ring systems can be aromatic, hydroaromatic and cyclic compounds joined by fusion. Fused ring systems comprise two, three or more rings. Depending on the way in which the rings are linked, a distinction is made in the case of fused ring systems between ortho-fusion, i.e. each ring shares an edge or two atoms with each adjacent ring, and peri-fusion in which one carbon atom belongs to more than two rings. Among fused ring systems, preference is given to ortho-fused ring systems.

The ligand/ligand pairs used according to the invention can be represented schematically by the formula I:

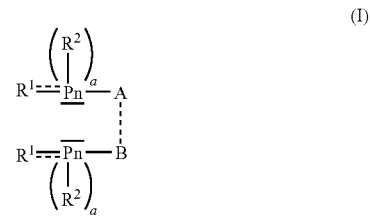

(I)

where the atoms Pn are independently selected pnicogen atoms or coordinating atoms of pseudopnicogen-comprising groups, A and B are radicals of mutually complementary functional groups between which there is a noncovalent interaction, $R^1$ is a singly or doubly bonded organyl radical, $R^2$ is a singly bonded organyl radical, a is, depending on the valence of the pnicogen atom or coordinating atom of the pseudopnicogen-comprising groups and the number of coordination sites occupied by the radical $R^2$, 0 or 1, where the pnicogen atom or coordinating atom of the pseudopnicogen-comprising group can, together with at least two of the radicals $R^1$, $R^2$ and A or B bound thereto, also be part of a ring system.

The Pn atoms in the formula I are preferably selected independently from among N, P, As, Sb and carbene carbon atoms.

In a first variant, the pnicogen- or pseudopnicogen-comprising group is a carbene group of the formula $R^1$—C—A or $R^1$—C—B. The carbene carbon atom is then preferably part of a ring system of the formula I.1

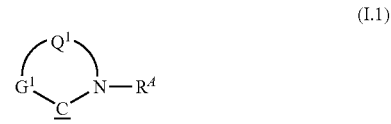

(I.1)

where $G^1$ is $NR^B$ or $CR^CR^D$, where $R^B$, $R^C$ and $R^D$ are each, independently of one another, hydrogen, alkyl, cycloalkyl, heterocycloalkyl, aryl or hetaryl, where $R^C$ or $R^D$ may also be one bond equivalent of a double bond, $Q^1$ is a divalent bridging group having from 1 to 5 atoms between the flanking bonds, $R^A$ is hydrogen, alkyl, cycloalkyl, heterocycloalkyl, aryl or hetaryl, where one of the radicals $R^A$, $R^B$, $R^C$, $R^D$ or a radical on the group $Q^1$ is a functional group capable of forming intermolecular, noncovalent bonds or comprises such a group.

The compounds of the formula I.1 are preferably selected from among the N-heterocyclic carbenes of the formulae I.1a to I.1d

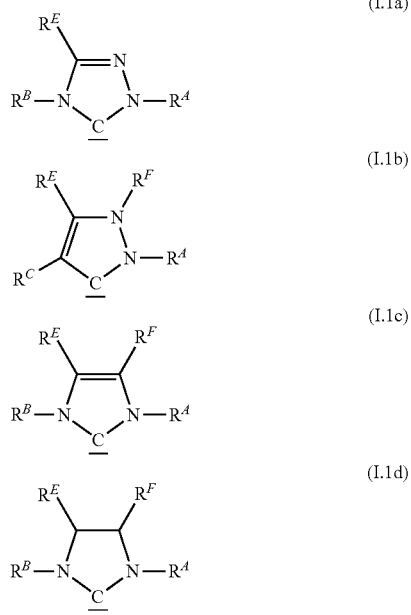

where
$R^A$, $R^B$, $R^C$, $R^E$ and $R^F$ are each, independently of one another, hydrogen, alkyl, cycloalkyl, heterocycloalkyl, aryl or hetaryl, where one of these radicals is a functional group capable of forming intermolecular, noncovalent bonds or comprises such a group.

In the compounds of the formulae I.1a to I.1d, the radicals $R^A$, $R^B$, $R^C$, $R^E$ and $R^F$ which are not a functional group capable of forming intermolecular, noncovalent bonds or comprise such a group are preferably unsubstituted or monosubstituted or polysubstituted alkyl or aryl radicals.

The radical $R^A$ in the compounds of the formulae I.1a to I.1d is preferably a functional group capable of forming intermolecular, noncovalent bonds or comprises such a group.

In a second variant, the pnicogen- or pseudopnicogen-comprising group is an imine group of the formula $R^1=N-A$ or $R^1=N-B$. The imine group is then preferably part of a ring system of the formula I.2

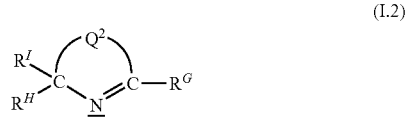

where
$Q^2$ is a divalent bridging group having from 1 to 5 atoms between the flanking bonds, and
$R^G$, $R^H$ and $R^I$ are each, independently of one another, hydrogen, alkyl, cycloalkyl, heterocycloalkyl, aryl or hetaryl, where one of the radicals $R^G$, $R^H$, $R^I$ or a radical on the group $Q^2$ is a functional group capable of forming intermolecular, noncovalent bonds or comprise such a group.

The group $Q^2$ in the formula I.2 is preferably a $C_1$-$C_5$-alkylene group which can contain a heteroatom or a heteroatom-comprising group, preferably selected from among O, S or $NR^K$ ($R^K$=hydrogen, alkyl, cycloalkyl, aryl).

The compounds of the formula I.2 are preferably selected from among cyclic imines of the formulae I.2a and I.2b

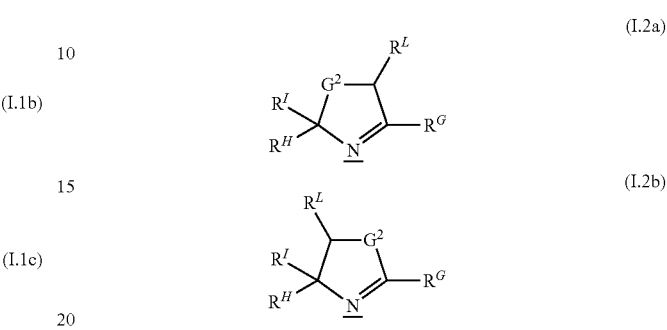

where
$G^2$ is O or $NR^K$, where $R^K$ is hydrogen, alkyl, cycloalkyl, heterocycloalkyl, aryl or hetaryl,
$R^G$, $R^H$, $R^I$ and $R^L$ are each, independently of one another, hydrogen, alkyl cycloalkyl, heterocycloalkyl, aryl or hetaryl, where one of the radicals $R^G$, $R^H$, $R^I$, $R^K$ and $R^L$ is a functional group capable of forming intermolecular, noncovalent bonds or comprises such a group.

The radical $R^G$ in the compounds of the formulae I.2a and I.2b is preferably a functional group capable of forming intermolecular, noncovalent bonds or comprises such a group.

The radical $R^H$ in the compounds of the formulae I.2a and I.2b is preferably alkyl, in particular methyl, ethyl, isopropyl or tert-butyl, aryl, in particular phenyl, or arylalkyl, in particular benzyl.

The radicals $R^I$ and $R^L$ in the compounds of the formulae I.2a and I.2b are preferably each hydrogen.

The group $G^2$ in the compounds of the formulae I.2a and I.2b is preferably O or $NR^K$.

In a third variant, the pnicogen- or pseudopnicogen-comprising group is selected from among groups of the formula I.3

where
Pn is N, P, As or Sb, preferably P,
$R^1$ and $R^2$ are each, independently of one another, alkyl, alkoxy, cycloalkyl, cycloalkoxy, heterocycloalkyl, heterocycloalkoxy, aryl, aryloxy, hetaryl or hetaryloxy or
$R^1$ and $R^2$ together with the phosphorus atom to which they are bound form a 4- to 8-membered heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, $COOR^c$, $COO^-M^+$, $SO_3R^c$, $SO_3^-$ $M^+$, $PO_3(R^c)(R^d)$, $(PO_3)^{2-}(M^+)_2$, $NE^4E^5$, $(NE^4E^5E^6)^+X^-$, $OR^e$, $SR^e$, $(CHR^fCH_2O)_yR^e$, $(CH_2O)_yR^e$, $(CH_2CH_2NE^4)_y$, $R^e$, halogen, nitro, acyl and cyano, where
  $R^c$ and $R^d$ are identical or different radicals selected from among hydrogen, alkyl, cycloalkyl. aryl and hetaryl,
  $R^e$, $E^4$, $E^5$, $E^6$ are identical or different radicals selected from among hydrogen, alkyl, cycloalkyl, aryl and hetaryl,
  $R^f$ is hydrogen, methyl or ethyl,
  $M^+$ is a cation equivalent,
  $X^-$ is an anion equivalent and
  y is an integer from 1 to 240.

In a first preferred embodiment, the radicals $R^1$ and $R^2$ in the groups of the formula I.3 are not bridged. $R^1$ and $R^2$ are then preferably selected, independently of one another, from among alkyl, cycloalkyl, aryl and hetaryl, as defined at the outset.

Preferably at least one $R^1$ and $R^2$ is aryl and more preferably both $R^1$ and $R^2$ are aryl. For example, one of the radicals $R^1$ and $R^2$ is then phenyl and the other is naphthyl or $R^1$ and $R^2$ are both phenyl or $R^1$ and $R^2$ are both naphthyl. Preferred naphthyl radicals are 1-naphthyl radicals.

In a further preferred embodiment, the radicals $R^1$ and $R^2$ in the groups of the formula I.3 are bridged. The pnicogen-comprising group is then preferably a group of the formula

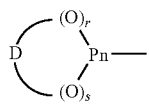

where
Pn is P, As or Sb, preferably P,
r and s are each. independently of one another, 0 or 1, and
D together with the phosphorus atom and the oxygen atom(s) to which it is bound forms a 4- to 8-membered heterocycle which may be fused with one, two or three cycloalkyl, heterocycloalkyl, aryl and/or hetaryl groups, where the fused-on groups may each independently of one another bear one, two, three or four substituents selected from among alkyl, alkoxy, halogen, sulfonate, $NE^4E^5$, alkylene-$NE^4E^5$, nitro, cyano and carboxylate, and/or D may bear one, two, three or four substituents selected from among alkyl, hydroxy, alkoxy, optionally substituted cycloalkyl and optionally substituted aryl, and/or D may be interrupted by 1, 2 or 3 optionally substituted heteroatoms.

The radical D is preferably a $C_2$-$C_6$-alkylene bridge which has 1 or 2 aryl groups fused onto it and/or may bear a substituent selected from among alkyl, optionally substituted cycloalkyl and optionally substituted aryl and/or may be interrupted by an optionally substituted heteroatom.

The fused-on aryls of the radicals D are preferably benzene or naphthalene. Fused-on benzene rings are preferably unsubstituted or have 1, 2 or 3, in particular 1 or 2, substituents which are preferably selected from among alkyl, alkoxy, halogen, sulfonate, $NE^4E^5$. alkylene-$NE^4E^5$, trifluoromethyl. nitro, carboxylate, alkoxycarbonyl, acyl and cyano. Fused-on naphthalenes are preferably unsubstituted or have 1, 2 or 3, in particular 1 or 2, of the substituents mentioned above in the case of the fused-on benzene rings in the ring which is not fused on and/or in the fused-on ring. In the case of the substituents on the fused-on aryls, alkyl is preferably $C_1$-$C_4$-alkyl and in particular methyl, isopropyl or tert-butyl. Alkoxy is preferably $C_1$-$C_4$-alkoxy and in particular methoxy. Alkoxycarbonyl is preferably $C_1$-$C_4$-alkoxycarbonyl.

If the $C_2$-$C_6$-alkylene bridge of the radical D is interrupted by 1, 2 or 3 optionally substituted heteroatoms, these are preferably selected from among O, S and $NR^h$, where $R^h$ is alkyl, cycloalkyl or aryl.

If the $C_2$-$C_6$-alkylene bridge of the radical D is substituted it preferably bears 1, 2, 3 or 4, in particular 2 or 4, substituents selected from among alkyl, alkoxy, hydroxy, cycloalkyl, heterocycloalkyl, aryl and hetaryl, where the cycloalkyl, heterocycloalkyl, aryl and hetaryl substituents may each bear 1, 2 or 3 of the substituents mentioned at the outset as being suitable for these radicals.

The radical D is preferably a $C_3$-$C_6$-alkylene bridge which, as indicated above, is fused and/or substituted and/or interrupted by optionally substituted heteroatoms. In particular, the radical D is a $C_3$-$C_6$-alkylene bridge which is fused with one or two phenyl and/or naphthyl groups, where the phenyl or naphthyl groups may bear 1, 2 or 3 of the abovementioned substituents.

Preference is given to the radical D together with the phosphorus atom and the oxygen atom(s) to which ft is bound forming a 4- to 8-membered heterocycle. In this case D is a radical selected from among the radicals of the formulae II.1 to II.4,

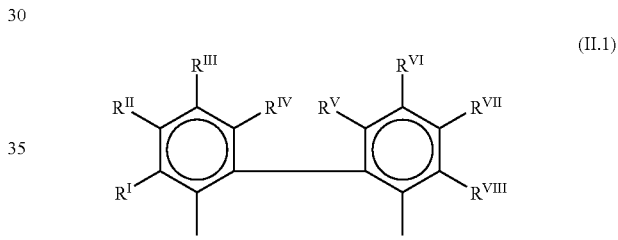

(II.1)

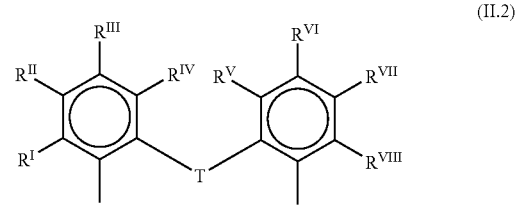

(II.2)

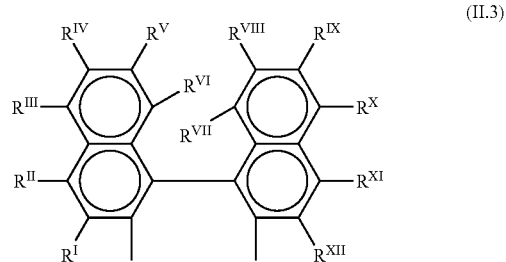

(II.3)

-continued

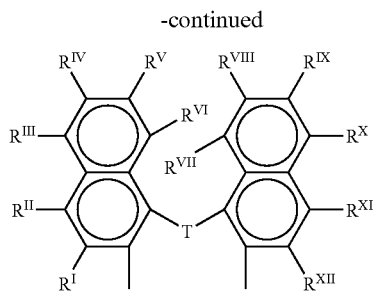
(II.4)

where

T is O, S or NR$^i$, where

R$^i$ is alkyl, cycloalkyl or aryl, or T is a C$_1$-C$_3$-alkylene bridge which may have a double bond and/or an alkyl, cycloalkyl or aryl substituent, where the aryl substituent may bear one, two or three of the substituents mentioned for aryl, or T is a C$_2$-C$_3$-alkylene bridge which is interrupted by O, S or NR$^i$, R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$ are each, independently of one another, hydrogen, alkyl, cycloalkyl, aryl, alkoxy, halogen, sulfonate, NE$^4$E$^5$, alkylene-NE$^4$E$^5$, trifluoromethyl, nitro, alkoxycarbonyl or cyano.

In a particularly preferred embodiment, the radicals R$^1$ and R$^2$ in the groups of the formula I.3 are bridged in such a way that the phosphorus-comprising group of the formula

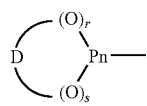

is a chiral heterocycle. The bridging groups D are then preferably selected from among groups of the formulae II.1 and II.3, where R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$ are each, independently of one another, hydrogen, alkyl, cycloalkyl, heterocycloalkyl, aryl, hetaryl, hydroxy, thiol. polyalkylene oxide, polyalkylenimine, alkoxy, halogen, SO$_3$H, sulfonate, NE$^4$E$^5$, alkylene-NE$^4$E$^5$, trifluoromethyl, nitro, alkoxycarbonyl, carboxyl, acyl and cyano, where E$^4$ and E$^5$ are identical or different radicals selected from among hydrogen, alkyl, cycloalkyl and aryl.

Preference is also given to Y being a group of the formula II.1 in which R$^{IV}$ and R$^V$ are each, independently of one another, C$_1$-C$_4$-alkyl or C$_1$-C$_4$-alkoxy. R$^{IV}$ and R$^V$ are preferably selected from among methyl, ethyl, isopropyl, tert-butyl and methoxy. In these compounds, R$^I$, R$^{II}$, R$^{III}$, R$^{VI}$, R$^{VII}$ and R$^{VIII}$ are preferably each hydrogen.

Preference is also given to Y being a group of the formula II.1 in which R$^I$ and R$^{VIII}$ are each, independently of one another, C$_1$-C$_4$-alkyl or C$_1$-C$_4$-alkoxy. R$^I$ and R$^{VIII}$ are particularly preferably tert-butyl. In these compounds, R$^{II}$, R$^{III}$, R$^{IV}$, R$^V$, R$^{VI}$, R$^{VII}$ are particularly preferably each hydrogen. Preference is also given to R$^{III}$ and R$^{VII}$ in these compounds being, independently of one another, C$_1$-C$_4$-alkyl or C$_1$-C$_4$-alkoxy. R$^{III}$ and R$^{VI}$ are particularly preferably selected independently from among methyl, ethyl, isopropyl, tert-butyl and methoxy.

Preference is also given to Y being a group of the formula II.1 in which R$^{II}$ and R$^{VII}$ are each hydrogen. In these compounds, preference is given to R$^I$, R$^{III}$, R$^{IV}$, R$^V$, R$^{VI}$ and R$^{VIII}$ each being, independently of one another, C$_1$-C$_4$-alkyl or C$_1$-C$_4$-alkoxy. R$^I$, R$^{III}$, R$^{IV}$, R$^V$, R$^{VI}$ and R$^{VIII}$ are particularly preferably selected independently from among methyl, ethyl, isopropyl, tert-butyl and methoxy.

Preference is also given to Y being a group of the formula II.3 in which R$^I$ to R$^{XII}$ are each hydrogen.

Preference is also given to Y being a group of the formula II.3 in which R$^I$ and R$^{XII}$ are each, independently of one another, C$_1$-C$_4$-alkyl or C$_1$-C$_4$-alkoxy. In particular, R$^I$ and R$^{XII}$ are selected independently from among methyl, ethyl, isopropyl, tert-butyl, methoxy and alkoxycarbonyl, preferably methoxycarbonyl. In these compounds, the radicals R$^{II}$ to R$^{XI}$ are particularly preferably each hydrogen.

Preferred chiral groups of the general formula I.3 include, for example, (2R,3S,4R, 5S)-2,5-dimethyl-3,4-dihydroxyphospholano and (2S,3R,4S,5R)-2,5-dimethyl-3,4-dihydroxyphospholano groups and also (R)-1,1'-binaphthylene-2,2'-diyldioxyphosphino, (S)-1,1'-binaphthylene-2,2'-diyldioxyphosphino, (S)-1,1'-biphenylene-2,2'-diyldioxyphosphino and (S)-1,1'-biphenylene-2,2'-diyldioxyphosphino groups which may be unsubstituted or, as described above, substituted.

Preference is given to at least one of the ligands used according to the invention having a functional group capable of tautomerism and capable of forming intermolecular non-covalent bonds. This group is preferably selected from among groups of the formula

and the tautomers thereof, where Y is O, S or NR$^4$ and R$^4$ is hydrogen, alkyl, cycloalkyl, heterocycloalkyl, aryl or hetaryl.

The position of the respective equilibrium between the tautomers is dependent, inter alia, on the group Y and on the substituents on the group capable of tautomerism. The equilibrium is shown below for the examples of keto-enol tautomerism and imine-enamine tautomerism:

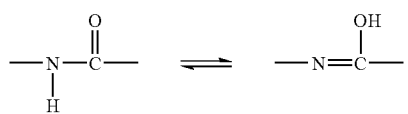

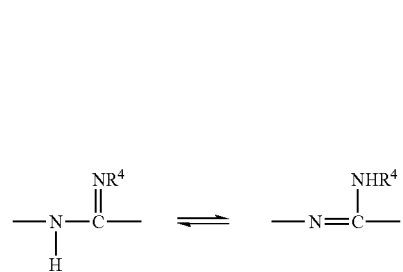

The ligands used according to the invention preferably comprise at least one structural element of the formula I.a or I.b

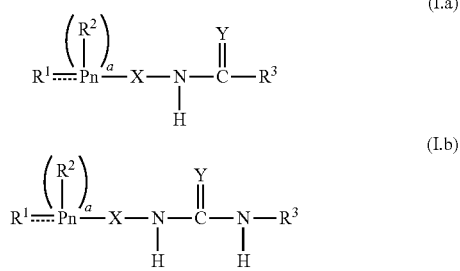

or tautomers thereof, where
Pn, $R^1$, $R^2$ and a are as defined above,
$R^3$ is hydrogen, alkyl, alkoxy, cycloalkyl, cycloalkoxy, heterocycloalkyl, heterocycloalkoxy, aryl, aryloxy, hetaryl or hetaryloxy,
X is a divalent bridging group having from 1 to 5 bridge atoms between the flanking bonds,
Y is O, S or $NR^4$, where $R^4$ is hydrogen, alkyl, cycloalkyl, heterocycloalkyl, aryl or hetaryl, where two or more of the radicals X and $R^1$ to $R^4$ together with the structural element of the formula I.a or I.b to which they are bound may form a monocyclic or polycyclic compound.

With regard to suitable and preferred radicals $R^1$ and $R^2$, reference is made to what has been said above.

In the compounds of the formulae I.a and I.b, Pn is preferably N, P, As or Sb, particularly preferably P, As or Sb and in particular P.

The divalent bridging group X in the compounds of the formulae I.a and I.b preferably has from 1 to 4, particularly preferably from 1 to 3, bridge atoms between the flanking bonds.

The divalent bridging group X is preferably a $C_1$-$C_5$-alkylene bridge which, depending on the number of bridge atoms, may have one or two double bonds and/or one, two, three or four substituents selected from among alkyl, cycloalkyl, heterocycloalkyl, aryl, hetaryl, carboxylate, sulfonate, phosphonate, $NE^1E^2$ ($E^1$, $E^2$=hydrogen, alkyl, cycloalkyl. acyl or aryl), hydroxy, thiol, halogen. nitro, acyl and cyano, where the cycloalkyl, aryl and hetaryl substituents may additionally bear one, two or three substituents selected from among alkyl, alkoxy, halogen, trifluoromethyl, nitro, alkoxycarbonyl and cyano, and/or one or two nonadjacent bridge atoms of the $C_1$-$C_5$-alkylene bridge X may be replaced by a heteroatom or a heteroatom-comprising group and/or the alkylene bridge X can have one or two aryl and/or hetaryl groups fused onto it, where the fused-on aryl and hetaryl groups may each bear one, two or three substituents selected from among alkyl, cycloalkyl, aryl, alkoxy, cycloalkoxy, aryloxy, acyl, halogen, trifluoromethyl, nitro, cyano, carboxyl, alkoxycarbonyl and $NE^1E^2$ ($E^1$ and $E^2$=hydrogen, alkyl, cycloalkyl, acyl or aryl) and/or two or more bridge atoms of the $C_1$-$C_5$-alkylene bridge X together with the structural element of the formula I.a or I.b to which they are bound may form a monocyclic or polycyclic compound.

X is preferably a $C_1$-$C_5$-alkylene bridge which can have one or two double bonds. Preference is also given to two or more of the bridge atoms of the bridge X together with the structural element of the formula I.a or I.b to which they are bound forming a monocyclic or polycyclic compound.

The ligands used according to the invention preferably have at least one structural element of the formula I.a or I.b in which the group X and the radical $R^3$ together with the group —NH—C(=Y)— to which they are bound form a 5- to 8-membered, preferably 6-membered ring. This ring can have one, two or three double bonds, where one of these double bonds can be due to the tautomeric group —N=C(YH)—. Preference is given to 6-membered rings which, allowing for the tautomerism, have three double bonds. Such ring systems in which one of the tautomers can form an aromatic ring system are particularly stable. The rings mentioned can be unsubstituted or can bear one, two, three, four or five of the abovementioned substituents. These are preferably selected from among $C_1$-$C_4$-alkyl, particularly preferably methyl, ethyl, isopropyl or tert-butyl, $C_1$-$C_4$-alkoxy, especially methoxy, ethoxy, isopropyloxy or tert-butyloxy, and aryl, preferably phenyl. In one useful embodiment, the rings mentioned have at least one double bond and the radicals bound to this double bond form a fused ring system having 1, 2 or 3 further rings. These are preferably benzene rings or naphthalene units. Fused-on benzene rings are preferably unsubstituted or have 1, 2 or 3 substituents selected from among alkyl, hydroxy, alkoxy, carboxylate, sulfonate, halogen, $NE^1E^2$, trifluoromethyl, nitro, alkoxycarbonyl, acyl and cyano. Fused-on naphthalene units are preferably unsubstituted or have 1, 2 or 3 of the substituents mentioned above in the case of the fused-on benzene rings in the ring which is not fused on and/or in the fused-on ring.

The ligands used according to the invention are preferably selected from among compounds of the formulae I.A to I.C

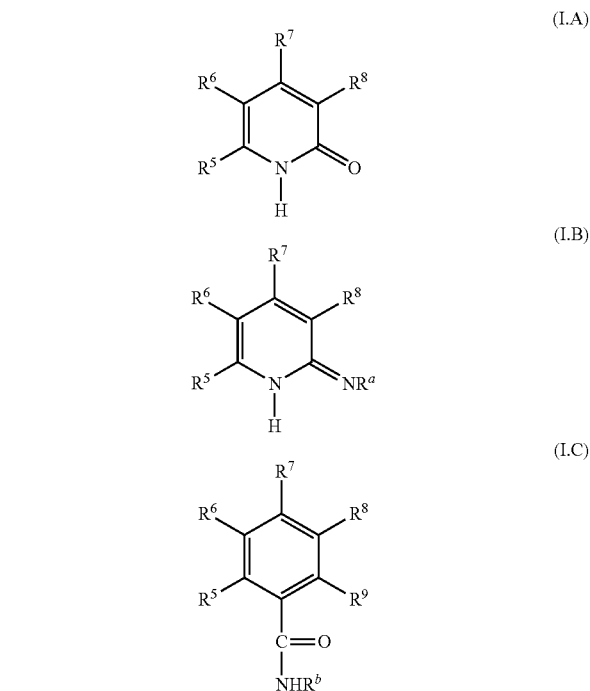

and the tautomers thereof, where one of the radicals $R^5$ to $R^9$ is a pnicogen- or pseudopnicogen-comprising group as defined above, the radicals $R^5$ to $R^9$ which are not a pnicogen- or pseudopnicogen-comprising group are each, independently of one another, hydrogen, alkyl, cycloalkyl, heterocycloalkyl, aryl, hetaryl, WCOOR°, WCOO⁻M⁺, W(SO₃)R°, W(SO₃)⁻M⁺, WPO₃(R°)(Rᵖ), W(PO₃)²⁻M⁺)₂, WNE¹E², W(NE¹E²E³)⁺X⁻, WORᵠ, WSRᵠ, (CHRʳCH₂O)ₓRᵠ, (CH₂NE¹)ₓRᵠ, (CH₂CH₂NE¹)ₓRᵠ, halogen, nitro, acyl or cyano, where W is a single bond, a heteroatom, a heteroatom-comprising group or a divalent bridging group having from 1 to 20 bridge atoms, R° and Rᵖ are identical or different radicals selected from among alkyl, cycloalkyl, acyl and aryl, Rᵠ, E¹, E², E³ are identical or different radicals selected from among hydrogen, alkyl, cycloalkyl, acyl and aryl, Rʳ is hydrogen, methyl or ethyl, M⁺ is a cation equivalent, X⁻ is an anion equivalent and x is an integer from 1 to 240, where two vicinal radicals R⁵ to R⁹ may also form a fused ring system, and Rᵃ and Rᵇ are each hydrogen, alkyl, cycloalkyl, heterocycloalkyl, aryl or hetaryl, and Rᵃ can also be acyl.

Suitable pnicogen- or pseudopnicogen-comprising groups of the compounds (I.A) to (I.C) are the groups I.1, I.2 and I.3 mentioned above. Suitable and preferred embodiments of these groups are incorporated by reference.

The pnicogen- or pseudopnicogen-comprising groups of the compounds (I.A) to (I.C) are preferably selected from among groups of the formula —W'-PnR¹R², where Pn is N, P, As or Sb, in particular P, As or Sb, especially P, W' is a single bond, a heteroatom, a heteroatom-comprising group or a divalent bridging group having from 1 to 4 bridge atoms between the flanking bonds, R¹ and R² are as defined above.

If two vicinal radicals selected from among the radicals R⁵ to R⁹ in the compounds of the formulae I.A to I.C which are not a pnicogen- or pseudopnicogen-comprising group form a fused ring system, these are preferably the radicals R⁷ and R⁸. The fused-on rings are preferably benzene rings or naphthalene units.

Fused-on benzene rings are preferably unsubstituted or have 1, 2 or 3 substituents which are preferably selected from among alkyl, hydroxy, alkoxy, carboxylate, sulfonate, halogen, NE¹E², trifluoromethyl, nitro, alkoxycarbonyl, acyl and cyano. Fused-on naphthalene units are preferably unsubstituted or have 1, 2 or 3 of the substituents mentioned above in the case of the fused-on benzene rings in the ring which is not fused on and/or in the fused-on ring.

When the radical Rᵃ in the compounds of the formula I.B is acyl, this acyl radical is preferably selected from among radicals of the formula —C(=O)—Rᵏ, where Rᵏ is hydrogen, alkyl, cycloalkyl, aryl or hetaryl. Rᵏ is preferably C₁-C₄-alkyl, in particular methyl, ethyl, n-propyl, isopropyl, n-butyl or tert-butyl. A preferred acyl radical Rᵃ is the pivaloyl radical.

The compounds of the formulae I.A to I.C are suitable as ligands in catalysts for asymmetric syntheses regardless of their ability to form intermolecular, noncovalent bonds. The invention therefore also provides a process for preparing chiral compounds by reacting a prochiral compound comprising at least one ethylenically unsaturated double bond with a substrate in the presence of a chiral catalyst comprising at least one transition metal complex with ligands selected from among compounds of the formulae I.A to I.C as defined above.

The ligands used according to the invention are preferably selected from among compounds of the formulae I.i to I.iii

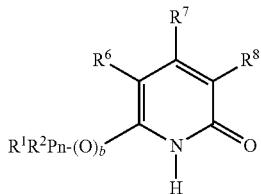

(I.i)

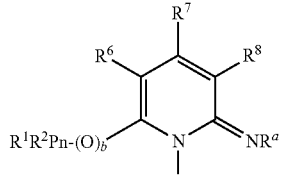

(I.ii)

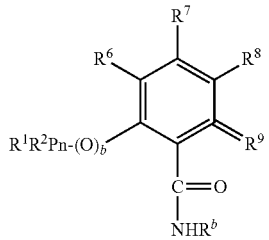

(I.iii)

and the tautomers thereof, where b is 0 or 1,

Pn is a pnicogen- or pseudopnicogen-comprising group, preferably N, P, As or Sb, in particular P, As or Sb, especially P, R¹ and R² are as defined above, R⁶ to R⁹ are each, independently of one another, hydrogen, C₁-C₄-alkyl, C₁-C₄-alkoxy, aryl, heteroaryl, acyl, halogen, C₁-C₄-alkoxycarbonyl or carboxylate, where two vicinal radicals R⁶ to R⁹ may also form a fused ring system, and Rᵃ and Rᵇ are each hydrogen, alkyl, cycloalkyl or aryl, and Rᵃ can also be acyl.

In the compounds of the formulae I.i to I.iii, the radicals R¹ and R² are preferably each, independently of one another, C₁-C₈-alkyl such as methyl, ethyl, isopropyl and tert-butyl, C₅-C₈-cycloalkyl such as cyclohexyl or aryl such as phenyl. Preference is given to both the radicals R¹ and R² being aryl. In particular, one of the radicals R¹ and R² is phenyl and the other is naphthyl or R¹ and R² are both phenyl or R¹ and R² are both naphthyl. Preferred naphthyl radicals are 1-naphthyl radicals.

Preference is also given to compounds of the formulae I.i to I.iii in which the radicals R¹ and R² are bridged so that they form a pnicogen-comprising group of the formula

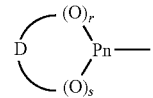

where Pn, D, r and s are as defined above.

In a particular embodiment, the pnicogen-comprising group is a chiral pnicogen-comprising group as described above. Reference is made to what has been said with regard to the groups II.1 and II.3.

The radicals $R^6$, $R^7$, $R^8$ and $R^9$ in the compounds I.i to I.iii are preferably selected independently from among hydrogen, $C_1$-$C_4$-alkyl, $C_1$-$C_4$-alkoxy, aryl, heteroaryl, carboxylate, sulfonate, $NE^1E^2$, halogen, trifluoromethyl, nitro, alkoxycarbonyl, acyl and cyano. $R^6$, $R^7$, $R^8$ and $R^9$ are preferably hydrogen, aryl or heteroaryl.

Preference is also given to the radicals $R^7$ and $R^8$ in the compounds I.i to I.iii forming a fused-on ring system.

In the compound of the formula I.ii, the radical $R^a$ is preferably hydrogen, $C_1$-$C_8$-alkyl. $C_5$-$C_8$-cycloalkyl or $C_8$-$C_{10}$-aryl. Preference is also given to the radical $R^a$ in the formula I.ii being acyl as defined above. In particular, $R^a$ is —C(=O)—$R^k$ where $R^k$=$C_1$-$C_4$-alkyl, in particular tert-butyl.

In the compounds of the formula I.iii the radical $R^b$ is preferably hydrogen, $C_1$-$C_8$-alkyl. $C_5$-$C_8$-cycloalkyl or $C_6$-$C_{10}$-aryl or hetaryl.

A preferred ligand of the formula I.i is

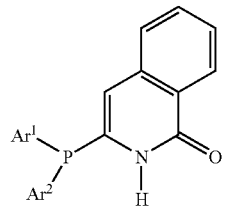

$Ar^1$, $Ar^2$=phenyl, phenyl 1-naphthyl, 1-naphthyl phenyl, 1-naphthyl and the tautomers thereof.

Preferred ligands of the formula I.ii are

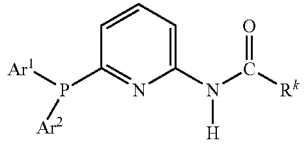

$Ar^1$, $Ar^2$=phenyl, phenyl 1-naphthyl, 1-naphthyl phenyl, 1-naphthyl $R^k$=methyl, ethyl, n-propyl, isopropyl, n-butyl, tert-butyl

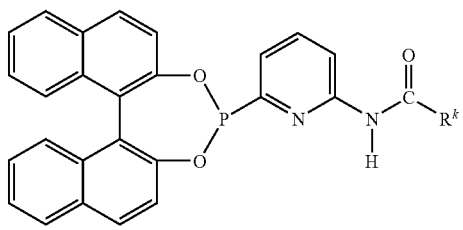

$R^k$=methyl, ethyl, n-propyl, isopropyl, n-butyl, tert-butyl and the tautomers thereof.

The ligand/ligand pairs according to the invention and those used according to the invention can be pairs of identical or different ligands.

Examples of ligands which can be used according to the invention are the following structures:

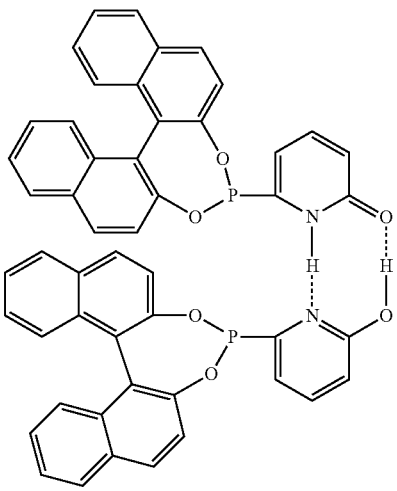

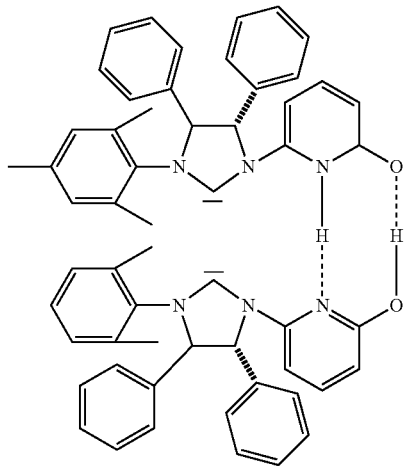

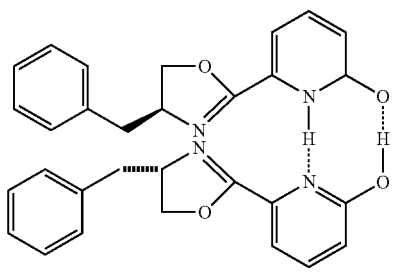

-continued
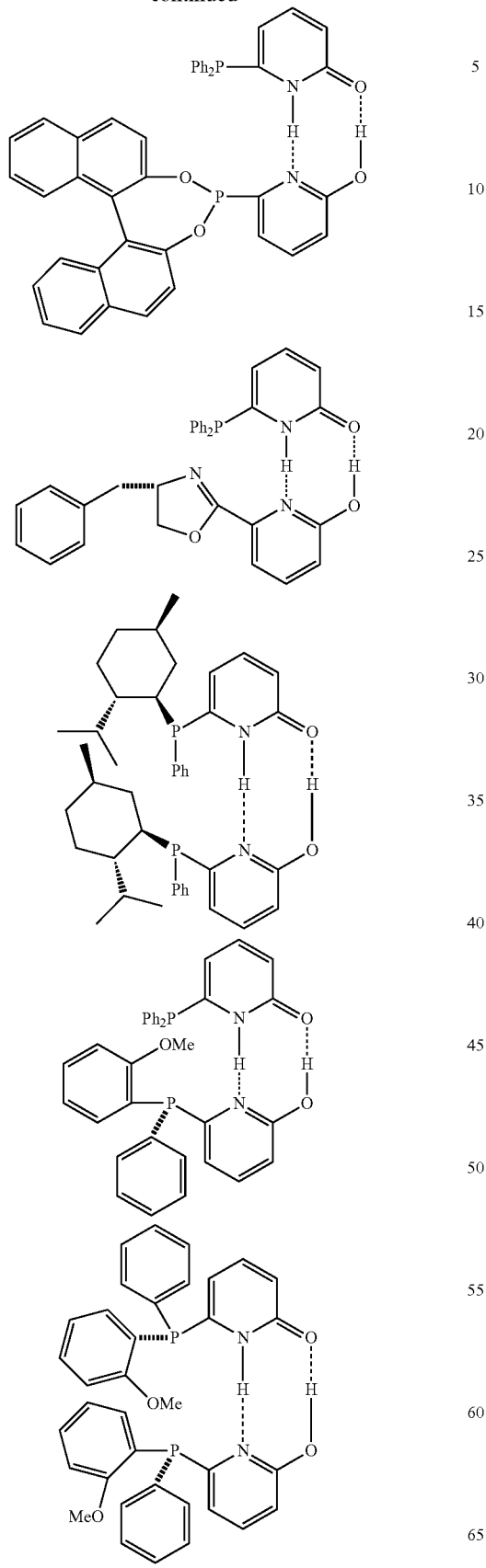
-continued
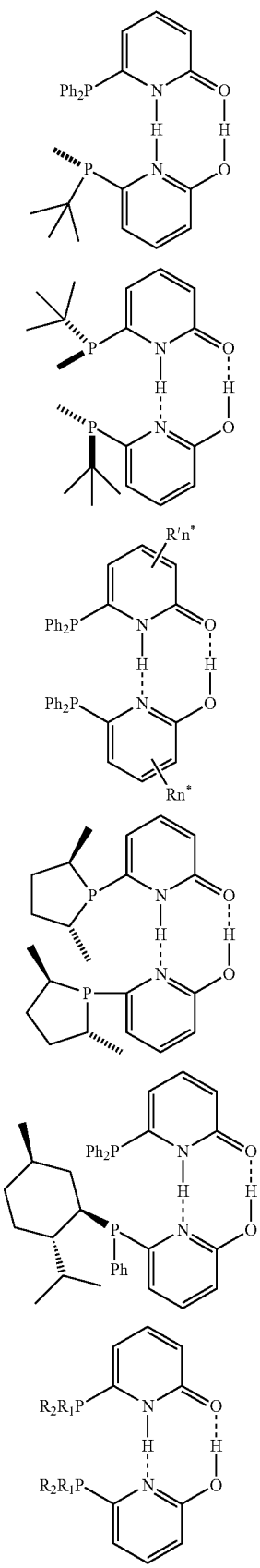

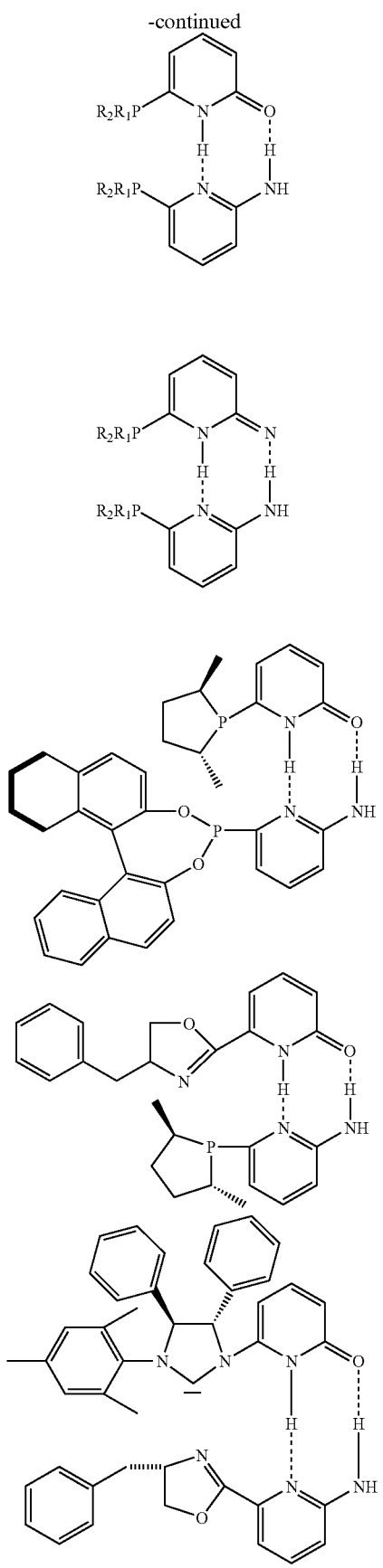
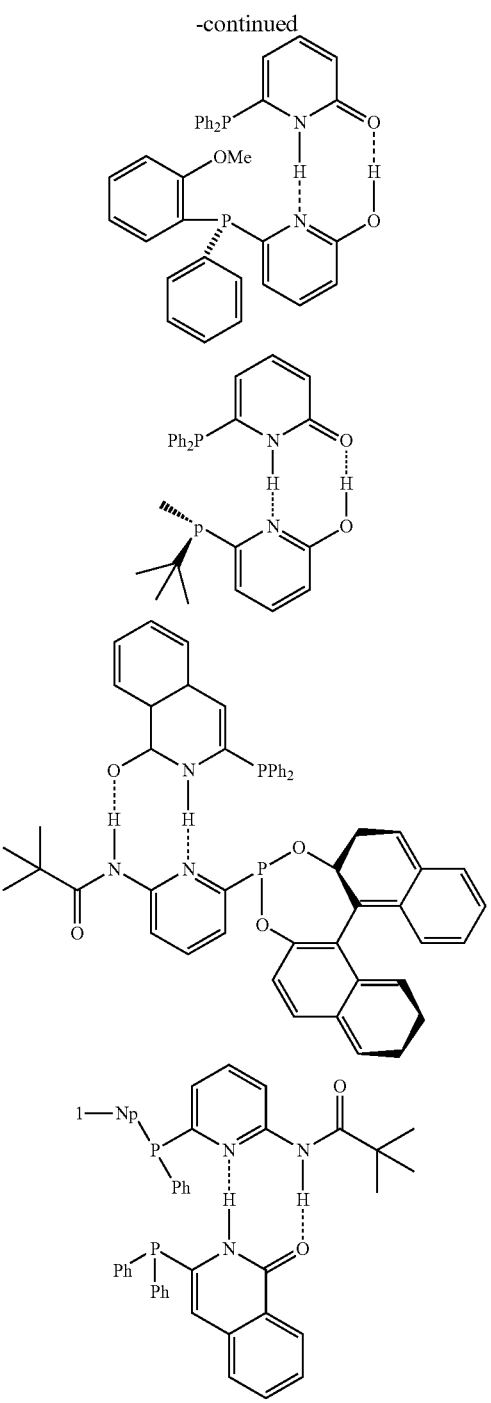

Examples of ligands which are preferred according to the invention are

6-[(R)-1,1'-binaphthylene-2,2'-diyldioxyphosphino]-1-H-pyridin-2-one,

6-[(S)-1,1'-binaphthylene-2,2'-diyldioxyphosphino]-1-H-pyridin-2-one, and 6-(3,5-dioxa-4-phosphacyclohepta[2,1-a,3,4-a]dinaphthalen-4-yloxy)-1H-pyridin-2-one.

The preparation of ligands which can be used according to the invention can be carried out by conventional methods known to those skilled in the art.

The invention further provides a chiral catalyst as described above. What has been said above with regard to suitable and preferred ligands is fully incorporated by reference at this point.

The chiral catalysts of the invention and those used according to the invention preferably comprise two or more of the above-described compounds as ligands. At least two of the ligands are preferably present in dimerized form (as ligand/ligand pairs). The ligand/ligand pairs can be made up of identical or different ligands. In addition to the ligands described above, they can further comprise at least one additional ligand which is preferably selected from among halides, amines, carboxylates, acetylacetonate, arylsulfonates and alkylsulfonates, hydride, CO, olefins, dienes, cycloolefins, nitriles, N-comprising heterocycles, aromatics and heteroaromatics, ethers, $PF_3$, phospholes, phosphabenzenes and monodentate. bidentate and polydentate phosphine, phosphinite, phosphonite, phosphoramidite and phosphite ligands.

The transition metal is preferably a metal of transition group I, VI, VI or VIII of the Periodic Table of the Elements. The transition metal is more preferably selected from among the metals of transition group VIII (i.e. Fe, Co, Ni, Ru, Rh, Pd, Os, Ir, Pt). In particular, the transition metal is iridium, nickel, ruthenium. rhodium, palladium or platinum.

The present invention provides a quite general process for preparing chiral compounds by reacting a prochiral compound comprising at least one ethylenically unsaturated double bond with a substrate in the presence of a chiral catalyst as described above. It is merely necessary for at least one of the ligands used or the overall catalytically active species to be chiral. In general, particular transition metal complexes are formed as catalytically active species under the reaction conditions of the individual processes for preparing chiral compounds. Thus, for example, the catalysts or catalyst precursors used in each case are converted under hydroformylation conditions into catalytically active species of the formula $H_xM_y(CO)_zL_q$, where M is a transition metal, L is a pnicogen-comprising compound and q, x, y, z are integers which depend on the valence and type of the metal and on the number of coordination sites occupied by the ligand L. It is preferred that z and q each have, independently of one another, a value of at least 1, e.g. 1, 2 or 3. The sum of z and q is preferably from 1 to 5. If desired, the complexes may further comprise at least one of the above-described additional ligands. There is reason to assume that the respective catalytically active species also comprises dimerized ligands (pseudochelates).

The catalytically active species is preferably present as a homogeneous single-phase solution in a suitable solvent. This solution can further comprise free ligand.

The process of the invention for preparing chiral compounds is preferably a hydrogenation, hydroformylation, hydrocyanation, carbonylation, hydroacylation (intramolecular and intermolecular), hydroamidation, hydroesterification, hydrosilylation, hydroboration, aminolysis (hydroamination), alcoholysis (hydroxy-alkoxy addition), isomerization, transfer hydrogenation, metathesis, cyclopropanation, aldol condensation, allylic alkylation or a [4+2]-cycloaddition (Diels-Alder reaction).

The process of the invention for preparing chiral compounds is more preferably a 1,2-addition, in particular a hydrogenation or a 1-hydro-2-carboaddition. For the purposes of the present invention, a 1,2-addition is an addition onto the two adjacent atoms of a C=X double bond (X=C, heteroatom). A 1-hydro-2-carboaddition is an addition reaction in which hydrogen is bound to one atom of the double bond and a carbon-comprising group is bound to the other after the reaction. Double bond isomerizations during the addition reaction are permitted. For the purposes of the present invention, the use of the term 1-hydro-2-carboaddition in the case of unsymmetrical substrates does not imply preferential addition of the carbon fragment onto the C2 atom, since the selectivity in respect of the orientation of the addition is generally dependent on the agent to be added on and the catalyst used. The term "1-hydro-2-carboaddition" is thus equivalent to "1-carbo-2-hydroaddition".

The reaction conditions of the process of the invention for preparing chiral compounds generally correspond, except for the chiral catalyst used, to those of the corresponding asymmetric processes. A person skilled in the art can thus find suitable reactors and reaction conditions for the respective process in the relevant literature and adapt them in a routine fashion. Suitable reaction temperatures are generally in a range from −100 to 500° C., preferably in a range from −80 to 250° C. Suitable reaction pressures are generally in a range from 0.0001 to 600 bar, preferably from 0.5 to 300 bar. The processes can generally be carried out continuously, semicontinuously or batchwise. Suitable reactors for a continuous reaction are known to those skilled in the art and are described, for example, in Ullmanns Enzyklopadie der technischen Chemie, Vol. 1, $3^{rd}$ edition, 1951, p. 743 ff. Suitable pressure-rated reactors are likewise known to those skilled in the art and are described, for example, in Ullmanns Enzyklopädie der technischen Chemie, Vol. 1, $3^{rd}$ edition, 1951, p. 769 ff.

The processes of the invention can be carried out in a suitable solvent which is inert under the respective reaction conditions. Generally suitable solvents are, for example, aromatics such as toluene and xylenes, hydrocarbons or mixtures of hydrocarbons. Further suitable solvents are halogenated, in particular chlorinated, hydrocarbons such as dichloromethane, chloroform or 1,2-dichloroethane. Further possible solvents are esters of aliphatic carboxylic acids with alkanols, for example ethyl acetate or Texanol®, ethers such as tert-butyl methyl ether, 1,4-dioxane and tetrahydrofuran and also dimethylformamide. In the case of sufficiently hydrophilic ligands, it is also possible to use alcohols such as methanol, ethanol, n-propanol, isopropanol, n-butanol, isobutanol. ketones such as acetone and methyl ethyl ketone, etc. Furthermore, "ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g. the tetrafluoroborates, acetates, tetrachloroaluminates, hexafluorophosphates, chlorides and tosylates. It is also possible to use a starting material, product or by-product of the respective reaction as solvent.

As prochiral ethylenically unsaturated compounds for the process of the invention, it is in principle possible to use all prochiral compounds which comprise one or more ethylenically unsaturated carbon-carbon or carbon-heteroatom double bonds. These include prochiral olefins in general (hydroformylation, intermolecular hydroacylation, hydrocyanation, hydrosilylation, carbonylation, hydroamidation, hydroesterification, aminolysis, alcoholysis, cyclopropanation, hydroboration, Diels-Alder reaction, metathesis), unsubstituted and substituted aldehydes (intramolecular hydroacylation, aldol condensation, allylic alkylation).

ketones (hydrogenation, hydrosilylation, aldol condensation, transfer hydrogenation, allylic alkylation) and imines (hydrogenation, hydrosilylation, transfer hydrogenation, Mannich reaction).

Suitable prochiral ethylenically unsaturated olefins are generally compounds of the formula

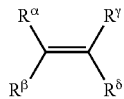

where $R^\alpha$ and $R^\beta$ and/or $R^\gamma$ and $R^\delta$ are radicals of different definitions. It is self-evident that to prepare chiral compounds according to the invention, the substrates reacted with the prochiral ethylenically unsaturated compound and sometimes also the stereoselectivity in respect of the addition of a particular substituent onto a particular carbon atom of the C—C double bond are chosen so that at least one chiral carbon atom results.

Subject to the abovementioned condition, $R^\alpha$, $R^\beta$, $R^\gamma$ and $R^\delta$ are preferably selected independently from among hydrogen, alkyl, cycloalkyl, heterocycloalkyl, aryl, hetaryl, alkoxy, cycloalkoxy, heterocycloalkoxy, aryloxy, hetaryloxy, hydroxy, thiol, polyalkylene oxide, polyalkylenimine, COOH, carboxylate, $SO_3H$, sulfonate, $NE^7E^8$, $NE^7E^8E^{9+}X^-$, halogen, nitro, acyl, acyloxy and cyano, where $E^7$, $E^8$ and $E^9$ are identical or different radicals selected from among hydrogen, alkyl, cycloalkyl and aryl and X is an anion equivalent, where the alkyl radicals may bear 1, 2, 3, 4, 5 or more substituents selected from among cycloalkyl, heterocycloalkyl, aryl, hetaryl, alkoxy, cycloalkoxy, heterocycloalkoxy, aryloxy, hetaryloxy, hydroxy, thiol, polyalkylene oxide. polyalkylenimine, COOH, carboxylate, $SO_3H$, sulfonate, $NE^{10}E^{11}$, $NE^{10}E^{11}E^{12+}X^-$, halogen, nitro. acyl, acyloxy and cyano, where $E^{10}$, $E^{11}$ and $E^{12}$ are identical or different radicals selected from among hydrogen, alkyl, cycloalkyl and aryl and $X^-$ is an anion equivalent, and the cycloalkyl, heterocycloalkyl, aryl and hetaryl radicals $R^\alpha$, $R^\beta$, $R^\gamma$ and $R^\delta$ each bear 1, 2, 3, 4, 5 or more substituents selected from among alkyl and the substituents mentioned above for the alkyl radicals $R^\alpha$, $R^\beta$, $R^\gamma$ and $R^\delta$, or two or more of the radicals $R^\alpha$, $R^\beta$, $R^\gamma$ and $R^\delta$ together with the C—C double bond to which they are bound form a monocyclic or polycyclic compound.

Suitable prochiral olefins are olefins which have at least 4 carbon atoms and terminal or internal double bonds and have a linear, branched or cyclic structure.

Suitable α-olefins are, for example 1-butene, 1-pentene, 1-hexene, 1-heptene, 1-octene, 1-nonene, 1-decene, 1-undecene, 1-dodecene, 1-octadecene etc.

Preferred linear (straight-chain) internal olefins are $C_4$-$C_{20}$-olefins such as 2-butene, 2-pentene, 2-hexene, 3-hexene, 2-heptene, 3-heptene, 2-octene, 3-octene, 4-octene etc.

Preferred branched, internal olefins are $C_4$-$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for the hydroformylation process are $C_5$-$C_8$-cycloalkenes such as cyclopentene, cyclohexene, cycloheptene, cyclooctene and their derivatives, e.g. their $C_1$-$C_{20}$-alkyl derivatives having from 1 to 5 alkyl substituents.

Olefins suitable for the hydroformylation process additionally include vinylaromatics such as styrene, α-methylstyrene, 4-isobutylstyrene, etc., 2-vinyl-6-methoxynaphthalene, 3-ethenylphenyl phenyl ketone, 4-ethenylphenyl 2-thienyl ketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, 2-propenylphenol, isobutyl-4-propenylbenzene, phenyl vinyl ether and cyclic enamides, e.g 2,3-dihydro-1,4-oxazines such as 2,3-dihydro-4-tert-butoxycarbonyl-1,4-oxazine. Further olefins suitable for the hydroformylation process are α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., vinyl chloride, allyl chloride, $C_3$-$C_{20}$-alkenols, -alkenediols and -alkadienols, e.g. allyl alcohol, hex-1-en4-ol, oct-1-en-4-ol, 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, vinylcyclohexene, dicyclopentadiene, 1,5,9-cyclooctatriene and also homopolymers and copolymers of butadiene.

Further prochiral ethylenically unsaturated compounds which are important as synthetic building blocks are, for example, p-isobutylstyrene, 2-vinyl-6-methoxynaphthalene, 3-ethenylphenyl phenyl ketone, 4-ethenylphenyl 2-thienyl ketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, 2-propenylphenol, isobutyl-4-propenylbenzene, phenyl vinyl ether and cyclic enamides, e.g. 2,3-dihydro-1,4-oxazines such as 2,3-dihydro-4-tert-butoxycarbonyl-1,4-oxazine.

The abovementioned olefins can be used individually or in the form of mixtures.

In a preferred embodiment, the chiral catalysts of the invention and those used according to the invention are prepared in situ in the reactor used for the reaction. However, if desired, the catalysts of the invention can also be prepared separately and isolated by customary methods. To prepare the catalysts of the invention in situ, it is possible to react, for example, at least one ligand used according to the invention, a compound or complex of a transition metal, if appropriate at least one further additional ligand and, if appropriate, an activating agent in an inert solvent under the conditions of the respective reaction (e.g. under hydroformylation conditions, hydrocyanation conditions, etc.). Suitable activating agents are, for example, Brönsted acids, Lewis acids such as $BF_3$, $AlCl_3$, $ZnCl_2$, and Lewis bases.

Suitable catalyst precursors are transition metals, transition metal compounds and transition metal complexes quite generally.

Suitable rhodium compounds or complexes are, for example, rhodium(II) and rhodium(III) salts such as rhodium (III) chloride, rhodium(III) nitrate, rhodium(II) sulfate, potassium rhodium sulfate, rhodium(II) or rhodium(II) carboxylate, rhodium(II) and rhodium(III) acetate, rhodium(III) oxide, salts of rhodic(III) acid, trisammonium hexachlororhodate(III), etc. Also suitable are rhodium complexes such as $Rh_4(CO)_{12}$, dicarbonylrhodium acetylacetonate, acetylacetonatobisethylenerhodium(I), etc.

Likewise suitable are ruthenium salts or compounds. Suitable ruthenium salts are, for example, ruthenium(II) chloride, ruthenium(IV), ruthenium(VI) or ruthenium(VIII) oxide, alkali metal salts of ruthenium oxo acids such as $K_2RuO_4$ or $KRuO_4$ or complexes such as $RuHCl(CO)(PPh_3)_3$, $(Ru(p\text{-}cymene)Cl)_2$, $(Ru(benzene)Cl)_2$, $(COD)R^a(methallyl)_2$, $Ru(acac)_3$. It is also possible to use the carbonyls of ruthenium such as dodecacarbonyltriruthenium or octadecacarbonylhexaruthenium, or mixed forms in which CO is partly replaced by ligands of the formula $PR_3$, e.g. $Ru(CO)_3(PPh_3)_2$, in the process of the invention.

Suitable iron compounds are, for example, iron(III) acetate and iron(II) nitrate and also the carbonyl complexes of iron.

Suitable nickel compounds are nickel fluoride and nickel sulfate. A nickel complex suitable for preparing a nickel catalyst is, for example, bis(1,5-cyclooctadiene)nickel(0).

Also suitable are carbonyl complexes of iridium and osmium, osmium halides, osmium octoate, palladium hydrides and halides, platinic acid, iridium sulfate, etc.

The abovementioned and further suitable transition metal compounds and complexes are known in principle and are adequately described in the literature or they can be prepared by a person skilled in the art using methods analogous to those for preparing the known compounds.

In general, the metal concentration in the reaction medium is in a range from about 1 to 10 000 ppm. The molar ratio of monopnicogen ligand to transition metal is generally in a range from about 0.5:1 to 1000:1, preferably from 1:1 to 500:1.

The use of supported catalysts is also useful. For this purpose, the above-described catalysts can be immobilized in an appropriate way, e.g. by binding via functional groups suitable as anchor groups, adsorption, grafting, etc., on a suitable support, e.g. glass, silica gel, synthetic resins, polymers, etc. They are then also suitable for use as solid state catalysts.

In a first preferred embodiment, the process of the invention is a hydrogenation (1,2-H,H-addition). In this case, a prochiral compound comprising at least one ethylenically unsaturated double bond is reacted with hydrogen in the presence of a chiral catalyst as described above to form corresponding chiral compounds having a single bond. Prochiral olefins give chiral carbon-comprising compounds, prochiral ketones give chiral alcohols and prochiral imines give chiral amines.

In a further preferred embodiment the process of the invention is a reaction with carbon monoxide and hydrogen, hereinafter referred to as hydroformylation.

The hydroformylation can be carried out in the presence of one of the above-mentioned solvents.

The molar ratio of mono(pseudo)pnicogen ligand to the metal of transition group VIII is generally in a range from about 1:1 to 1000:1, preferably from 2:1 to 500:1.

Preference is given to a process in which the hydroformylation catalyst is prepared in situ by reacting at least one ligand which can be used according to the invention, a compound or a complex of a transition metal and, if appropriate, an activating agent in an inert solvent under the hydroformylation conditions.

The transition metal is preferably a metal of transition group VIII of the Periodic Table of the Elements, particularly preferably cobalt, ruthenium, iridium, rhodium or palladium. Particular preference is given to using rhodium.

The composition of the synthesis gas comprising carbon monoxide and hydrogen which is used in the process of the invention can vary within wide limits. The molar ratio of carbon monoxide to hydrogen is generally from about 5:95 to 70:30, preferably from about 40:60 to 60:40. Particular preference is given to using a molar ratio of carbon monoxide to hydrogen in the region of about 1:1.

The temperature in the hydroformylation reaction is generally in a range from about 20 to 180° C., preferably from about 50 to 150° C. The pressure is generally in a range from about 1 to 700 bar, preferably from 1 to 600 bar, in particular from 1 to 300 bar. The reaction pressure can be varied as a function of the activity of the novel hydroformylation catalyst used. In general, the novel catalysts based on phosphorus-comprising compounds permit a reaction in a low-pressure range, for instance in the range from 1 to 100 bar.

The hydroformylation catalysts used according to the invention and those of the invention can be separated from the product from the hydroformylation reaction by customary methods known to those skilled in the art and can generally be reused for the hydroformylation.

Asymmetric hydroformylation by the process of the invention proceeds with a high stereoselectivity. Advantageously, the catalysts of the invention and those used according to the invention generally also display a high regioselectivity. Furthermore, the catalysts generally have a high stability under the hydroformylation conditions, so that longer catalyst operating lives can generally be achieved when using them than when using catalysts based on conventional chelating ligands known from the prior art. Advantageously, the catalysts of the invention and those used according to the invention also display a high activity, so that the respective aldehydes or alcohols are generally obtained in good yields.

A further important 1-hydro-2-carbo addition is the reaction with hydrogen cyanide, hereinafter referred to as hydrocyanation.

The catalysts used for hydrocyanation also comprise complexes of a metal of transition group VIII, in particular cobalt, nickel, ruthenium, rhodium, palladium, platinum, preferably nickel, palladium or platinum and very particularly preferably nickel. The preparation of the metal complexes can be carried out as described above. These same applies to the in situ preparation of the hydrocyanation catalysts of the invention. Hydrocyanation processes are described in J. March, Advanced Organic Chemistry, $4^{th}$ edition, pp. 811-812, which is hereby incorporated by reference.

In a further preferred embodiment, the 1-hydro-2-carbo addition is a reaction with carbon monoxide and at least one compound having a nucleophilic group, hereinafter referred to as carbonylation.

The carbonylation catalysts, too, comprise complexes of a metal of transition group VIII, preferably nickel, cobalt, iron, ruthenium, rhodium or palladium, in particular palladium. The preparation of the metal complexes can be carried out as described above. The same applies to the in situ preparation of the carbonylation catalysts of the invention.

The compounds having a nucleophilic group are preferably selected from among water, alcohols, thiols, carboxylic esters, primary and secondary amines.

A preferred carbonylation reaction is the conversion of olefins into carboxylic acids by means of carbon monoxide and water (hydrocarboxylation).

The carbonylation can be carried out in the presence of activating agents. Suitable activating agents are, for example, Brönsted acids, Lewis acids, e.g. $BF_3$, $AlCl_3$, $ZnCl_2$, and Lewis bases.

A further important 1,2-addition is hydroacylation. In asymmetric intramolecular hydroacylation, unsaturated aldehydes are converted into optically active cyclic ketones. In the case of asymmetric intermolecular hydroacylation, a prochiral olefin is reacted with an acyl halide in the presence of a chiral catalyst as described above to form a chiral ketone. Suitable hydroacylation processes are described in J. March, Advanced Organic Chemistry, 4$^{th}$ edition, p. 811, which is hereby incorporated by reference.

A further important 1,2-addition is hydroamidation. Here, a prochiral compound comprising at least one ethylenically unsaturated double bond is reacted with carbon monoxide and ammonia or a primary or secondary amine in the presence of a chiral catalyst as described above to form a chiral amide.

A further important 1,2-addition is hydroesterification. Here, a prochiral compound comprising at least one ethylenically unsaturated double bond is reacted with carbon monoxide and an alcohol in the presence of a chiral catalyst as described above to form a chiral ester.

A further important 1,2-addition is hydroboration. Here, a prochiral compound comprising at least one ethylenically unsaturated double bond is reacted with borane or a source of borane in the presence of a chiral catalyst as described above to form a chiral trialkylborane which can be oxidized to a primary alcohol (e.g. using NaOH/$H_2O_2$) or to a carboxylic acid. Suitable hydroboration processes are described in J. March, Advanced Organic Chemistry, 4$^{th}$ edition, pp. 783-789, which is hereby incorporated by reference.

A further important 1,2-addition is hydrosilylation. Here, a prochiral compound comprising at least one ethylenically unsaturated double bond is reacted with a silane in the presence of a chiral catalyst as described above to form a chiral compound functionalized with silyl groups. Prochiral olefins result in chiral alkanes functionalized with silyl groups. Prochiral ketones result in chiral silyl ethers or alcohols. In the hydrosilylation catalysts, the transition metal is preferably selected from among Pt, Pd, Rh, Ru and Ir. Here, it can be advantageous to use combinations or mixtures of one of the abovementioned catalysts with further catalysts. Suitable additional catalysts include, for example, platinum in finely divided form ("platinum black"), platinum chloride and platinum complexes such as hexachloroplatinic acid or divinyidisiloxane-platinum complexes, e.g. tetramethyldivinyidisiloxane-platinum complexes. Suitable rhodium catalysts are, for example, RhCl(P($C_6H_5$)$_3$)$_3$ and RhCl$_3$. Also suitable are RuCl$_3$ and IrCl$_3$. Further suitable catalysts are Lewis acids such as AlCl$_3$ or TiCl$_4$ and also peroxides.

Suitable silanes are, for example, halogenated silanes such as trichlorosilane. methyldichlorosilane, dimethylchlorosilane and trimethylsiloxydichlorosilane; alkoxysilanes such as trimethoxysilane, triethoxysilane, methyldimethoxysilane, phenyldimethoxysilane, 1,3,3,5,5,7,7-heptamethyl-1,1-dimethoxytetrasiloxane and also acyloxysilanes.

The reaction temperature in the silylation is preferably in a range from 0 to 140° C., particularly preferably from 40 to 120° C. The reaction is usually carried out under atmospheric pressure, but can also be carried out at superatmospheric pressures, e.g. in the range from about 1.5 to 20 bar, or subatmospheric pressures, e.g. from 200 to 600 mbar.

The reaction can be carried out without solvent or in the presence of a suitable solvent. Preferred solvents are, for example, toluene, tetrahydrofuran and chloroform.

A further important 1,2-addition is aminolysis (hydroamination). Here, a prochiral compound comprising at least one ethylenically unsaturated double bond is reacted with ammonia or a primary or secondary amine in the presence of a chiral catalyst as described above to form a chiral primary, secondary or tertiary amine. Suitable hydroamination processes are described in J. March, Advanced Organic Chemistry, 4$^{th}$ edition, pp. 768-770, which is hereby incorporated by reference.

A further important 1,2-addition is alcoholysis (hydroalkoxy-addition). Here, a prochiral compound comprising at least one ethylenically unsaturated double bond is reacted with an alcohol in the presence of a chiral catalyst as described above to form a chiral ether. Suitable alcoholysis processes are described in J. March. Advanced Organic Chemistry, 4$^{th}$ edition, pp. 763-764, which is hereby incorporated by reference.

A further important reaction is isomerization. Here, a prochiral compound comprising at least one ethylenically unsaturated double bond is converted in the presence of a chiral catalyst as described above into a chiral compound.

A further important reaction is cyclopropanation. Here, a prochiral compound comprising at least one ethylenically unsaturated double bond is reacted with a diazo compound in the presence of a chiral catalyst as described above to form a chiral cyclopropane.

A further important reaction is metathesis. Here, a prochiral compound comprising at least one ethylenically unsaturated double bond is reacted with a further olefin in the presence of a chiral catalyst as described above to form a chiral hydrocarbon.

A further important reaction is aldol condensation. Here, a prochiral ketone or aldehyde is reacted with a silylenol ether in the presence of a chiral catalyst as described above to form a chiral aldol.

A further important reaction is allylic alkylation. Here, a prochiral ketone or aldehyde is reacted with an allylic alkylating agent in the presence of a chiral catalyst as described above to form a chiral hydrocarbon.

A further important reaction is [4+2]-cycloaddition. Here, a diene is reacted with a dienophile, with at least one of these compounds being prochiral, in the presence of a chiral catalyst as described above to form a chiral cyclohexene compound.

The invention further provides for the use of catalysts comprising at least one complex of a metal of transition group VIII with at least one ligand as described above for hydroformylation, hydrocyanation, carbonylation, hydroacylation, hydroamidation, hydroesterification, hydrosilylation, hydroboration, hydrogenation, aminolysis, alcoholysis, isomerization, metathesis, cyclopropanation or [4+2]-cycloaddition.

The process of the invention is suitable for preparing many useful optically active compounds. The process stereoselectively generates a chiral center. Examples of optically active compounds which can be prepared by the process of the invention are substituted and unsubstituted alcohols or phenols, amines, amides, esters, carboxylic acids or anhydrides, ketones, olefins, aldehydes, nitriles and hydrocarbons. Optically active aldehydes which are preferably prepared by the asymmetric hydroformylation process of the invention comprise, for example, S-2-(p-isobutylphenyl)propionaldehyde, S-2-(6-methoxynaphthyl)propionaldehyde, S-2-(3-benzoylphenyl)propionaldehyde, S-2-(p-thienoylphenyl)propionaldehyde. S-2-(3-fluoro-4-phenyl)phenylpropionaidehyde, S-2-[4-(1,3-dihydro-1-oxo-2H-isoindol-2-yl)phenyl]propionaldehyde, S-2-(2-methylacetaldehyde)-5-benzoylthiophene, etc. Further optically active compounds which can be prepared by the process of the invention (including possible formation of a derivative) are described in Kirk- Othmer, Encyclopedia of Chemical Technology, Third Edition, 1984, and The Merck Index, An Encyclopedia of Chemicals, Drugs and Biologicals, Eleventh Edition, 1989, which are hereby incorporated by reference.

The process of the invention makes it possible to prepare optically active products with high enantioselectivity and, if necessary, regioselectivity. e.g. in hydroformylation. Enantiomeric excesses (ee) of at least 50%, preferably at least 75% and particularly preferably at least 90% can be achieved.

The products obtained are isolated by customary methods known to those skilled in the art. These include, for example, solvent extraction, crystallization, distillation, evaporation, e.g. in a wiped film evaporator or falling film evaporator, etc.

The optically active compounds obtained by the process of the invention can be subjected to one or more subsequent reaction(s). Such processes are known to those skilled in the art. They include, for example, the esterification of alcohols, the oxidation of alcohols to aldehydes, N-alkylation of amides, addition of aldehyde onto amides, nitrile reduction, acylation of ketones with esters, acylation of amines, etc. For example, optically active aldehydes obtained by asymmetric hydroformylation according to the invention can be subjected to oxidation to form carboxylic acids, reduction to form alcohols, aldol condensation to form α,β-unsaturated compounds, reductive amination to form amines, amination to form imines, etc.

A preferred derivative-forming reaction comprises oxidation of an aldehyde prepared by the asymmetric hydroformylation process of the invention to form the corresponding optically active carboxylic acid. Many pharmaceutically important compounds such as S-ibuprofen, S-naproxen, S-ketoprofen, S-suprofen, S-fluorobiprofen, S-indoprofen, S-tiaprofenic acid, etc, can be prepared in this way.

Olefin starting materials, aldehyde intermediates and end products are listed in the following table for some preferred derivative-forming reactions:

| Olefin | Aldehyde | Product |
| --- | --- | --- |
| p-Isobutylstyrene | S-2-(p-Isobutylphenyl)propionaldehyde | S-Ibuprofen |
| 2-Vinyl-6-methoxynaphthalene | S-2-(6-Methoxynaphthyl)propionaldehyde | S-Naproxen |
| 3-Ethenylphenyl phenyl ketone | S-2-(3-Benzoylphenyl)propionaldehyde | S-Ketoprofen |
| 4-Ethenylphenyl 2-thienyl ketone | S-2-(p-Thienoylphenyl)propionaldehyde | S-Suprofen |
| 4-Ethenyl-2-fluorobiphenyl | S-2-(3-Fluoro-4-phenyl)phenylpropionaldehyde | S-Fluorobiprofen |
| 1,3-Dihydro-1-oxo-2H-isoindol-2-yl)styrene | S-2-(4-(1,3-Dihydro 1-oxo-2H-isoindol-2-yl)phenyl)-propionaldehyde | S-Indoprofen |
| 2-Ethenyl-5-benzoylthiophene | S-2-(2-Methylacetaldehyd)-5-benzoylthiophene | S-Tiaprofenic acid |
| 3-Ethenylphenyl phenyl ether | S-2-(3-Phenoxy)propionaldehyde | S-Fenoprofen |
| Propenylbenzene | S-2-Phenylbutyraldehyde | S-Phenetamide, S-Butetamate |
| Isobutyl-4-propenylbenzene | S-2-(4-Isobutylphenyl)butyraldehyde | S-Butibufen |
| Phenyl vinyl ether | S-2-Phenoxypropionaldehyde | Pheneticillin |
| Vinyl chloride | S-2-Chloropropionaldehyde | S-2-Chloropropionic acid |
| 2-Vinyl-6-methoxynaphthalene | S-2-(6-Methoxynaphthyl)propionaldehyde | 5-Naproxol |
| 2-Vinyl-6-methoxynaphthalene | S-2-(6-Methoxynaphthyl)propionaldehyde | S-Naproxen (Na salt) |
| 5-(4-Hydroxy)benzoyl-3H-pyrrolizine | 5-(4-Hydroxy)benzoyl-1-formyl-2,3-dihydropyrrolizine | Ketorolac or derivatives |
| tert-Butyl 2.3-dihydro[1,4]oxazine-4-carboxylate | tert-Butyl 3-formylmorpholine-4-carboxylate | tert-Butyl 3-hydroxymethylmorpholine-4-carboxylate |
| 2,3-Dihydro[1,4]oxazine-4-carbaldehyde | Morpholine-3,4-dicarbaldehyde | 3-Hydroxymethylmorpholine-4-carbaldehyde |
| 1-Phenylvinyl acetate | 1-phenylvinyl acetate | 3-Methylamino-1-phenylpropyl acetate |

EXAMPLES

Example 1

Preparation of 6-(1-naphthylphenylphosphino)-2-pivaloylaminopyridine (6-NPPAP)

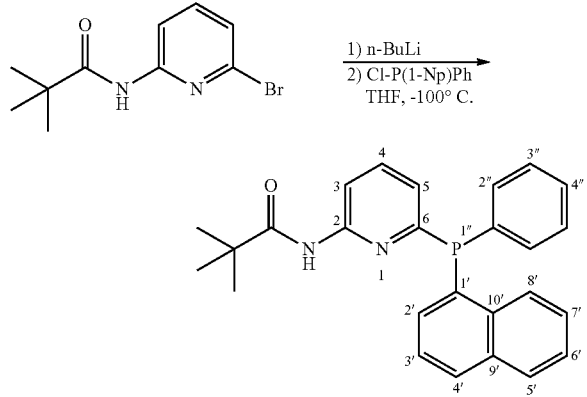

n-Butyllithium (8.7 ml, 14.0 mmol, 1.6 M solution in hexane, 2 eq) was added to a solution of 2-bromo-6-N-pivaloylaminopyridine (1.80 g, 7.0 mmol) in tetrahydrofuran (30 ml) at −100° C. over a period of 20 minutes and the reaction solution was stirred at this temperature for 1 hour. After addition of chloro(1-naphthyl)phenylphosphine (1.89 g, 7.0 mmol, 1 eq, prepared as described by G. Wittig et al., in Justus Liebig Ann. Chem. 1971, 17-26), the reaction solution was warmed to room temperature over a period of 12 hours. The reaction was stopped by addition of saturated $NaHCO_3$ solution (30 ml), the aqueous phase was separated off and extracted with ethyl acetate (3 20 ml). The combined organic phases were dried over $MgSO_4$ and the solvent was removed on a rotary evaporator. The crude product was purified by column chromatography using silica gel as stationary phase and a cyclohexane/ethyl acetate mixture (10:1).

The title compound (1.50 g, 3.6 mmol, 52%) could be isolated in the form of a white solid.

Mp: 55° C.

$^1$H-NMR (499.873 MHz, $C_6D_6$):

δ=0.86 (s, 9H, $CH_3$), 6.66 (d, J=7.5 Hz, 1H, H5), 6.93 (td, J=7.5 Hz, J=1.9 Hz, 1H, H4), 7.04-7.05 (m, 3H, Ar—H), 7.11 (t, J=7.7 Hz, 1H, Ar—H), 7.17-7.19 (m, 2H, Ar—H), 7.27-7.30 (m, 1H, Ar—H), 7.43-7.47 (m, 2H, Ar—H), 7.57-7.60 (m, 2H, Ar—H), 7.92 (br, 1H, NH), 8.51 (d, J=7.5 Hz, 1H, H3), 8.75-8.77 (m, 1H, Ar—H).

$^{13}$C-NMR (125.709 MHz, $C_6D_6$):

δ=27.1 (s, 3C, $C(CH_3)_3$), 39.5 (s, 1C, $C(CH_3)_3$), 112.8 (s, 1C, C3), 124.5 (d, $J_{C,P}$=11.8 Hz, 1C, C5), 126.0 (d, $J_{C,P}$=1.8 Hz, 1C, Ar—C), 126.4 (d, $J_{C,P}$=1.5 Hz, 1C, Ar—C), 126.6 (s, 1C, Ar—C), 126.7 (d, $J_{C,P}$=18.1 Hz, 1C, Ar—C), 128.9 (d, $J_{C,P}$=7.3 Hz, 2C, C3"), 129.0 (s, 1C, Ar—C), 129.3 (s, 1C, Ar—C), 130.0 (s, 1C, Ar—C), 132.9 (d, $J_{C,P}$=1.2 Hz, 1C, C4), 134.0 (d, $J_{C,P}$=4.2 Hz, 1C, C9"), 134.4 (d, $J_{C,P}$=15.1 Hz, 1C, C1' or C1"), 135.1 (d, $J_{C,P}$=20.6 Hz, 2C, C2"), 136.0 (d, $J_{C,P}$=10.9 Hz, 1C, C1' or C1"), 136.33 (d, $J_{C,P}$=22.1 Hz, 1C, C10'), 138.2 (d, $J_{C,P}$=1.5 Hz, 1C, Ar—C), 152.8 (d, $J_{C,P}$=15.1 Hz, 1C, C2 or C6), 161.9 (d, $J_{C,P}$=6.4 Hz, 1C, C2 or C6), 176.5 (s, 1C, C=O).

$^{31}$P-NMR (121.468 MHz, $CDCl_3$):

δ=−13.72 (s)

Chiral HPLC (AD-H, n-heptane/EtOH 70:30, RT, 0.8 ml/min, 295 nm, RT)

| | | |
|---|---|---|
| (−)-enantiomer: | 5.7 min | $[α]_D$ = −38° (c = 0.30, $CHCl_3$, 21° C.) |
| (+)-enantiomer: | 6.8 min | $[α]_D$ = +37° (c = 0.52, $CHCl_3$, 21° C.) |

The resolution of 200 mg of rac-6-NPPAP was carried out by means of preparative HPLC (Chiralpak AD-H, n-heptane/EtOH 70:30, RT, 11.0 ml/min, 295 nm), with the individual enantiomers being obtained in a purity of ee >99%.

Example 2

Preparation of a Heterodimeric Pt Complex

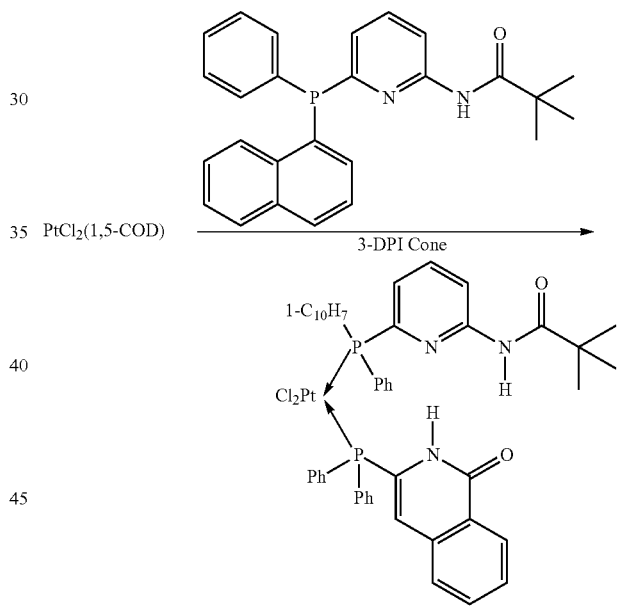

A solution of 3-diphenylphosphino-2H-isoquinolin-1-one (3-DPICone) (12.6 mg, 3.82×10$^{-2}$ mmol, 1 eq) and 6-NPPAP from example 1 (14.4 mg. 3.28 10$^2$ mmol, 1 eq) in $CDCl_3$ (0.4 ml) was added to a solution of $PtCl_2$(1,5-cyclooctadiene) (14.3 mg, 3.82 10$^{-2}$ mmol, 1 eq) in $CDCl_3$ (0.4 ml). The formation of the heteroleptic complex was observed by means of low-temperature NMR spectroscopy.

$^{31}$P-NMR 294K (121.468 MHz, $CDCl_3$):

δ=6.36 (bd. $^1J_{P1-P}$=3521 Hz), 8.02 (bd, $^1J_{P1-P}$=3756 Hz).

$^1$H-NMR 240K (499.873 MHz, $CDCl_3$):

δ=1.11 (s, 9H, $CH_3$), 6.69-6.74 (m, 2H, Ar—H), 6.88 (t, J=7.2 Hz, 1H, Ar—H), 7.17-7.27 (m, 7H, Ar—H), 7.34-7.48 (m, 5H, Ar—H), 7.55-7.72 (m, 6H, Ar—H), 7.79 (d, J=8.0 Hz, 1H), 7.81 (d, J=7.9 Hz, 1H), 7.87-7.89 (br, 1H, Ar—H), 7.98 (d, J=7.7 Hz, 1H), 8.04-8.08 (m, 3H, Ar—H), 8.24 (t,

J=8.4 Hz, 2H, Ar—H), 10.44 (s, 1H, NH), 11.53 (d, J=5.8 Hz, NH).

$^{31}$P-NMR 240K (121.468 MHz, CDCl$_3$):

δ=6.36 (dd, $^1J_{Pt-P}$=3515 Hz, $^2J_{P-P}$=13.2 Hz), 7.26 (dd, $^1J_{P1-P}$=3753 Hz, $^2J_{P-P}$=13.2 Hz).

Example 3

Asymmetric hydrogenation of methyl 2-acetamidoacrylate

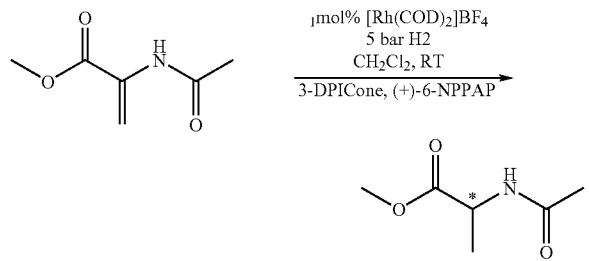

A mixture of [Rh(COD)$_2$]BF$_4$ (2 mg, 5.0 10$^{-3}$ mmol, 1.0 mol %), 3-DPICone (2.1 mg, 6.4 10$^{-3}$ mmol, 1.3 mol %) and (+)-6-NPPAP from example 1 (2.7 mg, 6.5 10$^{-3}$ mmol, 1.3 mol %) was dissolved in dry and degassed CH$_2$Cl$_2$ (5 ml) and stirred at room temperature for 10 minutes. The catalyst solution was admixed with methyl 2-acetamidoacrylate (71.6 mg, 0.5 mmol) and the solution was transferred to a steel autoclave. The autoclave was flushed five times with hydrogen and subsequently brought to a pressure of 5 bar at room temperature for 48 hours.

After the reaction was complete, the conversion was determined by means of $^1$H-NMR spectroscopy and the enantiomeric excess was determined by means of chiral GC (Hydrodex β-TBDAc).

The conversion was quantitative, and the enantiomeric excess was 43% (R).

Example 4

Preparation of a chiral phosphonite derivative of 6-DPPAP a) Synthesis of 6-(bis(diethylamino)phosphino)-2-pivaloylaminopyridine

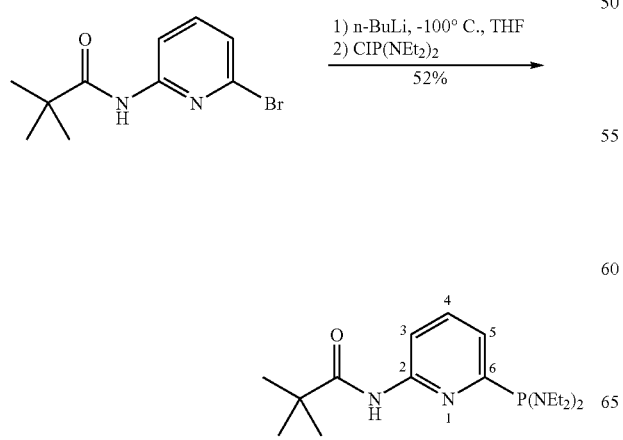

2-Bromo-6-N-pivaloylaminopyridine (1.98 g, 7.7 mmol, 1 eq) was dissolved in tetrahydrofuran (50 ml). At −100° C., n-butyllithium (10.0 ml, 1.54 M in hexane, 15.4 mmol, 2 eq) was slowly added dropwise. The yellow solution was stirred at −100° C. for 90 minutes. Bis(diethylamino)chlorophosphane, prepared as described by J. Sakai, W. B. Schweizer, D. Seebach in Helv. Chim. Acta 1993, 76, 2654-2665 (1.62 g, 7.7 mmol, 1 eq), was then added quickly. The reaction mixture was subsequently warmed to room temperature overnight. The solvent was taken off under reduced pressure, the residue was taken up in diethyl ether (30 ml) and admixed with degassed water (0.14 g, 0.14 ml, 7.8 mmol, 1 eq). The suspension formed was filtered through Celfte and magnesium sulfate under a protective gas atmosphere. The solvent was removed at reduced pressure. The crude product was purified by means of bulb tube distillation at 200° C. (10$^{-3}$ mbar). The title compound was obtained as a viscous, colorless liquid (1.41 g, 4.0 mmol, 52%).

$^1$H-NMR (300.064 MHz, C$_6$D$_6$):

δ=1.05 (s, 9H, C(CH)$_3$), 1.10 (t, 12H, J=7.0 Hz, CH$_2$CH$_3$), 3.07 (m, 8H, CH$_2$CH$_3$), 7.25 (d, 2H, J=3.1 Hz, Ar—H), 8.01 (b, 1H, NH), 8.48 (dd, 1H, J=5.0 Hz, J=4.0 Hz, Ar—H).

$^{13}$C-NMR (100.620 MHz, C$_6$D$_6$):

δ=14.9 (s, 3C, C(CH)$_3$), 27.3 (s, 4C, CH$_2$CH$_3$), 39.6 (s, 1C, C(CH)$_3$), 43.9 (d, 4C, J$_{P,C}$=17.4 Hz, CH$_2$CH$_3$), 111.6 (d, 1C, J$_{P,C}$=2.9 Hz, Ar—CH), 122.8 (d, 1C, J$_{P,C}$=21.8 Hz, C5), 137.6 (s, 1C, Ar—CH), 152.4 (d, 1C, J$_{P,C}$=7.3 Hz, Ar—C), 164.8 (d, 1C, J$_{P,C}$=13.1 Hz, Ar—C), 176.1 (s, iC, C=O).

$^{31}$P-NMR (121.468 MHz, C$_5$D$_6$):

δ=94.3 (s)

b) Synthesis of 6-(3,5-dioxa-4-phosphacyclohepta[2,1-a; 3,4-a']dinaphthalen-4-yl)-2-pivaloylaminopyridine

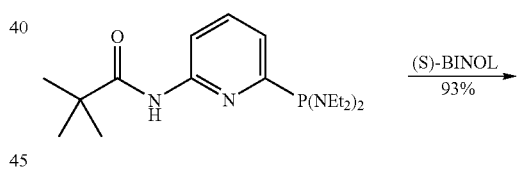

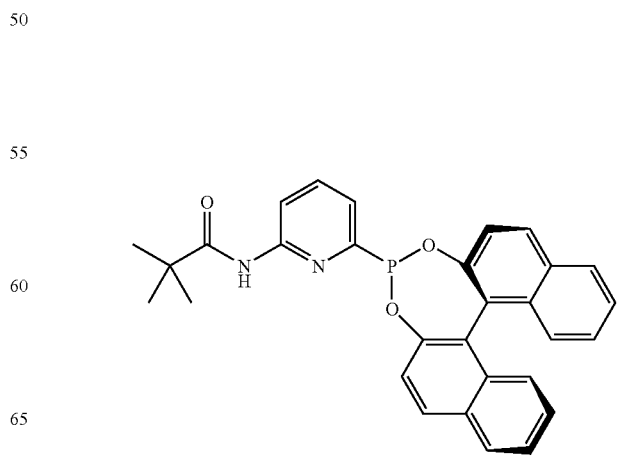

N-(6-(bis(diethylamino)phosphino)pyridin-2-yl)pivalamide (0.292 g, 0.60 mmol, 1 eq) was dissolved in toluene (12 ml). (S)-BINOL (0.172 g, 0.60 mmol, 1 eq) was subsequently added and the reaction mixture was refluxed for 3 hours. The solvent was removed under reduced pressure. The title compound could be obtained in the form of a white solid (0.276 g, 0.56 mmol, 93%).

$^1$H-NMR (300.064 MHz, CDCl$_3$):

δ=1.37 (s, 9H, C(CH$_3$)$_3$), 6.71 (d, 1H; J=8.8 Hz, Ar—H), 6.98 (d, 1H, J=7.5 Hz, Ar—H), 7.15-7.47 (m, 7H, Ar—H), 7.62 (pt, 2H, J=8.9 Hz, Ar—H), 7.83 (d, 1H, J=8.1 Hz, Ar—H), 7.96 (d, 1H, J=8.0 Hz, Ar—H), 8.04 (d, 1H, J=8.8 Hz, Ar—H), 8.16 (b, 1H, NH), 8.27 (d, 1H, J=8.5 Hz, Ar—H).

$^{31}$P-NMR (121.468 MHz, CDCl$_3$):

δ=167.2 (s)

Example 5

Preparation of a Heterodimeric Pt Complex

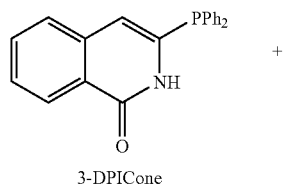
3-DPICone

+

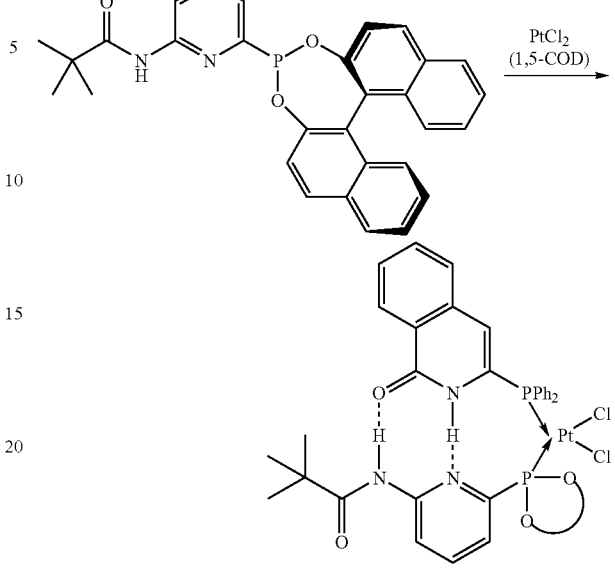

A solution of 3-DPICone (8.8 mg, 2.67 10$^{-2}$ mmol, 1 eq) and aminopyridine ligand (13.2 mg, 2.67 10$^{-2}$ mmol, 1 eq) in CDCl$_3$ (0.4 ml) was added to a solution of PtCl$_2$(1.5-cyclooctadiene) (10.0 mg, 2.67 10$^{-2}$ mmol, 1 eq) in CDCl$_3$ (0.4 ml). The formation of the heteroleptic complex was observed by means of NMR spectroscopy.

$^{31}$P-NMR (121.468 MHz, CDCl$_3$).

δ=17.2 (dd, $^1J_{P1-P}$=3590 Hz, $^2J_{P-P}$=13.4 Hz). 108.0 (d, $^2J_{P-P}$=13.4 Hz).

| Olefin | Aldehyde | Product |
| --- | --- | --- |
| p-Isobutylstyrene | S-2-(p-Isobutylphenyl)propionaldehyde | S-Ibuprofen |
| 2-Vinyl-6-methoxynaphthalene | S-2-(6-Methoxynaphthyl)propionaldehyde | S-Naproxen |
| 3-Ethenylphenyl phenyl ketone | S-2-(3-Benzoylphenyl)propionaldehyde | S-Ketoprofen |
| 4-Ethenylphenyl 2-thienyl ketone | S-2-(p-Thienoylphenyl)propionaldehyde | S-Suprofen |
| 4-Ethenyl-2-fluorobiphenyl | S-2-(3-Fluoro-4-phenyl)phenylpropionaldehyde | S-Fluorobiprofen |
| 1,3-Dihydro-1-oxo-2H-isoindol-2-yl)styrene | S-2-(4-(1,3-Dihydro 1-oxo-2H-isoindol-2-yl)phenyl)-propionaldehyde | S-Indoprofen |
| 2-Ethenyl-5-benzoylthiophene | S-2-(2-Methylacetaldehyd)-5-benzoylthiophene | S-Tiaprofenic acid |
| 3-Ethenylphenyl phenyl ether | S-2-(3-Phenoxy)propionaldehyde | S-Fenoprofen |
| Propenylbenzene | S-2-Phenylbutyraldehyde | S-Phenetamide, S-Butetamate |
| Isobutyl-4-propenylbenzene | S-2-(4-Isobutylphenyl)butyraldehyde | S-Butibufen |
| Phenyl vinyl ether | S-2-Phenoxypropionaldehyde | Pheneticillin |
| Vinyl chloride | S-2-Chloropropionaldehyde | S-2-Chloropropionic acid |
| 2-Vinyl-6-methoxynaphthalene | S-2-(6-Methoxynaphthyl)propionaldehyde | S-Naproxol |
| 2-Vinyl-6-methoxynaphthalene | S-2-(6-Methoxynaphthyl)propionaldehyde | S-Naproxen (Na salt) |
| 5-(4-Hydroxy)benzoyl-3H-pyrrolizine | 5-(4-Hydroxy)benzoyl-1-formyl-2,3-dihydropyrrolizine | Ketorolac or derivatives |
| tert-Butyl 2,3-dihydro[1,4]oxazine-4-carboxylate | tert-Butyl 3-formylmorpholine-4-carboxylate | tert-Butyl 3-hydroxymethylmorpholine-4-carboxylate |
| 2,3-Dihydro[1,4]oxazine-4-carbaldehyde | Morpholine-3,4-dicarbaldehyde | 3-Hydroxymethylmorpholine-4-carbaldehyde |
| 1-Phenylvinyl acetate | 1-phenylvinyl acetate | 3-Methylamino-1-phenylpropyl acetate |

EXAMPLES

Example 1

Preparation of 6-(1-naphthylphenylphosphino)-2-pivaloylaminopyridine (6-NPPAP)

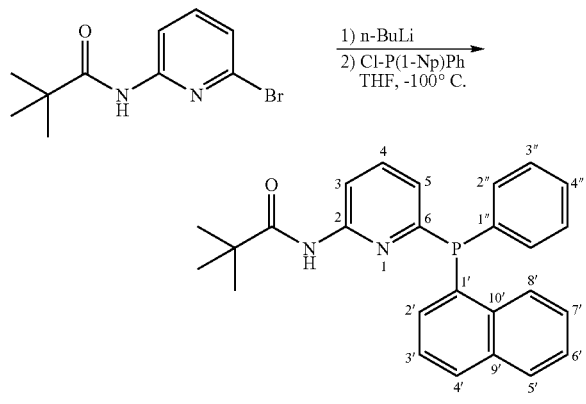

n-Butyllithium (8.7 ml, 14.0 mmol, 1.6 M solution in hexane, 2 eq) was added to a solution of 2-bromo-6-N-pivaloylaminopyridine (1.80 g, 7.0 mmol) in tetrahydrofuran (30 ml) at −100° C. over a period of 20 minutes and the reaction solution was stirred at this temperature for 1 hour. After addition of chloro(1-naphthyl)phenylphosphine (1.89 g, 7.0 mmol, 1 eq, prepared as described by G. Wittig et al., in Justus Liebig Ann. Chem. 1971, 17-26), the reaction solution was warmed to room temperature over a period of 12 hours. The reaction was stopped by addition of saturated $NaHCO_3$ solution (30 ml), the aqueous phase was separated off and extracted with ethyl acetate (3×20 ml). The combined organic phases were dried over $MgSO_4$ and the solvent was removed on a rotary evaporator. The crude product was purified by column chromatography using silica gel as stationary phase and a cyclohexane/ethyl acetate mixture (10:1).

The title compound (1.50 g, 3.6 mmol, 52%) could be isolated in the form of a white solid.

Mp: 55° C.

$^1$H-NMR (499.873 MHz, $C_6D_6$):

δ=0.86 (s, 9H, $CH_3$), 6.66 (d, J=7.5 Hz, 1H, H5), 6.93 (td, J=7.5 Hz, J=1.9 Hz, 1H, H4), 7.04-7.05 (m, 3H, Ar—H), 7.11 (t, J=7.7 Hz, 1H, Ar—H), 7.17-7.19 (m, 2H, Ar—H), 7.27-7.30 (m, 1H, Ar—H), 7.43-7.47 (m, 2H, Ar—H), 7.57-7.60 (m, 2H, Ar—H), 7.92 (br, 1H, NH), 8.51 (d, J=7.5 Hz, 1H, H3), 8.75-8.77 (m, 1H, Ar—H).

$^{13}$C-NMR (125.709 MHz, $C_6D_6$): δ=27.1 (s, 3C, C($CH_3$)$_3$), 39.5 (s, 1C, C($CH_3$)$_3$), 112.8 (s, 1C, C3), 124.5 (d, $J_{C,P}$=11.8 Hz, 1C, C5), 126.0 (d, $J_{C,P}$=1.8 Hz, 1C, Ar—C), 126.4 (d, $J_{C,P}$=1.5 Hz, 1C, Ar—C), 126.6 (s, 1C, Ar—C), 126.7 (d, $J_{C,P}$=18.1 Hz, 1C, Ar—C), 128.9 (d, $J_{C,P}$=7.3 Hz, 2C, C3"), 129.0 (s, 1C, Ar—C), 129.3 (s, 1C, Ar—C), 130.0 (s, 1C, Ar—C), 132.9 (d, $J_{C,P}$=1.2 Hz, 1C, C4), 134.0 (d, $J_{C,P}$=4.2 Hz, 1C, C9'), 134.4 (d, $J_{C,P}$=15.1 Hz, 1C, C1' or C1"), 135.1 (d, $J_{C,P}$=20.6 Hz, 2C, C2"), 136.0 (d, $J_{C,P}$=10.9 Hz, 1C, C1' or C1"), 136.33 (d, $J_{C,P}$=22.1 Hz, 1C, C10'), 138.2 (d, $J_{C,P}$=1.5 Hz, 1C, Ar—C), 152.8 (d, $J_{C,P}$=15.1 Hz, 1C, C2 or C6), 161.9 (d, $J_{C,P}$=6.4 Hz, 1C, C2 or C6), 176.5 (s, 1C, C=O).

$^{31}$P-NMR (121.468 MHz, $CDCl_3$):

δ=−13.72 (s)

Chiral HPLC (AD-H, n-heptane/EtOH 70:30, RT, 0.8 ml/min, 295 nm, RT)

| | | |
|---|---|---|
| (−)-enantiomer: | 5.7 min | $[\alpha]_D$= −38° (c = 0.30, $CHCl_3$, 21° C.) |
| (+)-enantiomer: | 6.8 min | $[\alpha]_D$= +37° (c = 0.52, $CHCl_3$, 21° C.) |

The resolution of 200 mg of rac-6-NPPAP was carried out by means of preparative HPLC (Chiralpak AD-H, n-heptane/EtOH 70:30, RT, 11.0 mL/min, 295 nm), with the individual enantiomers being obtained in a purity of ee >99%.

Example 2

Preparation of a Heterodimeric Pt Complex

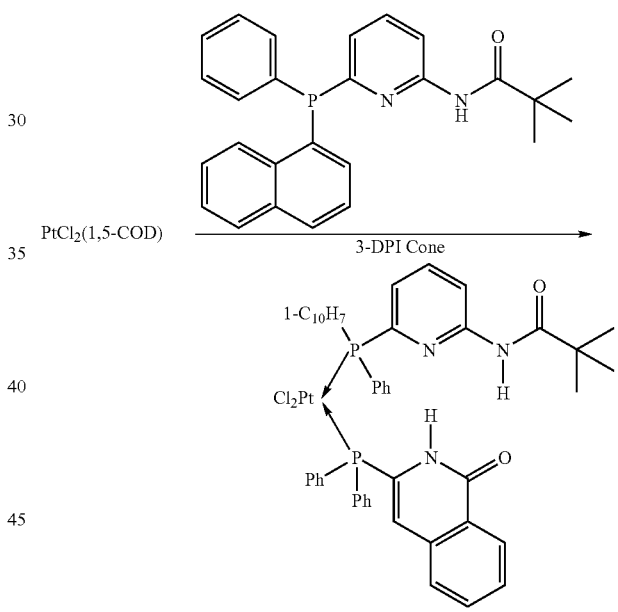

A solution of 3-diphenylphosphino-2H-isoquinolin-1-one (3-DPICone) (12.6 mg, 3.82×10$^{-2}$ mmol, 1 eq) and 6-NPPAP from example 1 (14.4 mg, 3.28×10$^2$ mmol, 1 eq) in $CDCl_3$ (0.4 ml) was added to a solution of $PtCl_2$(1,5-cyclooctadiene) (14.3 mg, 3.82×10$^{-2}$ mmol, 1 eq) in $CDCl_3$ (0.4 ml). The formation of the heteroleptic complex was observed by means of low-temperature NMR spectroscopy.

$^{31}$P-NMR 294K (121.468 MHz, $CDCl_3$):

δ=6.36 (bd, $^1J_{P1-P}$=3521 Hz), 8.02 (bd, $^1J_{P1-P}$=3756 Hz).

$^1$H-NMR 240K (499.873 MHz, $CDCl_3$):

δ=1.11 (s, 9H, $CH_3$), 6.69-6.74 (m, 2H, Ar—H), 6.88 (t, J=7.2 Hz, 1H, Ar—H), 7.17-7.27 (m, 7H, Ar—H), 7.34-7.48 (m, 5H, Ar—H), 7.55-7.72 (m, 6H, Ar—H), 7.79 (d, J=8.0 Hz, 1H), 7.81 (d, J=7.9 Hz, 1H), 7.87-7.89 (br, 1H, Ar—H), 7.98 (d, J=7.7 Hz, 1H), 8.04-8.08 (m, 3H, Ar—H), 8.24 (t,

J=8.4 Hz, 2H, Ar—H), 10.44 (s, 1H, NH), 11.53 (d, J=5.8 Hz, NH).

$^{31}$P-NMR 240K (121.468 MHz, CDCl$_3$,):

δ=6.36 (dd, $^1J_{P1\text{-}P}$=3515 Hz, $^2J_{P\text{-}P}$=13.2 Hz), 7.26 (dd, $^1J_{Pt\text{-}P}$=3753 Hz, $^2J_{P\text{-}P}$=13.2 Hz).

Example 3

Asymmetric Hydrogenation of Methyl 2-acetamidoacrylate

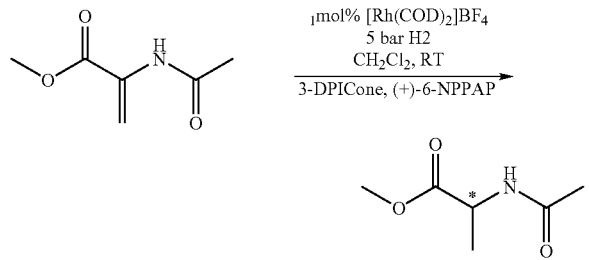

A mixture of [Rh(COD)$_2$]BF$_4$ (2 mg, 5.00 10$^{-3}$ mmol, 1.0 mol %), 3-DPICone (2.1 mg, 6.4×10$^{-3}$ mmol, 1.3 mol %) and (+)-6-NPPAP from example 1 (2.7 mg, 6.5×10$^{-3}$ mmol, 1.3 mol %) was dissolved in dry and degassed CH$_2$Cl$_2$ (5 ml) and stirred at room temperature for 10 minutes. The catalyst solution was admixed with methyl 2-acetamidoacrylate (71.6 mg, 0.5 mmol) and the solution was transferred to a steel autoclave. The autoclave was flushed five times with hydrogen and subsequently brought to a pressure of 5 bar at room temperature for 48 hours.

After the reaction was complete, the conversion was determined by means of $^1$H-NMR spectroscopy and the enantiomeric excess was determined by means of chiral GC (Hydrodex β-TBDAc).

The conversion was quantitative, and the enantiomeric excess was 43% (R).

Example 4

Preparation of a chiral phosphonite derivative of 6-DPPAP a) Synthesis of 6-(bis(diethylamino)phosphino)-2-pivaloylaminopyridine

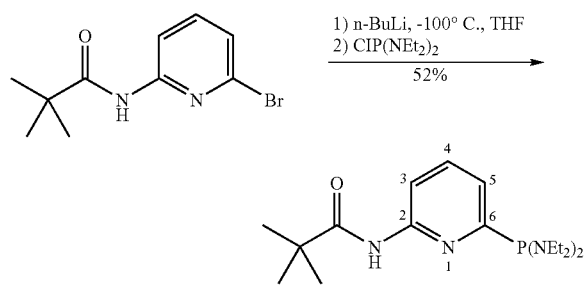

2-Bromo-6-N-pivaloylaminopyridine (1.98 g, 7.7 mmol, 1 eq) was dissolved in tetrahydrofuran (50 ml). At −100° C., n-butyllithium (10.0 ml, 1.54 M in hexane, 15.4 mmol, 2 eq) was slowly added dropwise. The yellow solution was stirred at −100° C. for 90 minutes. Bis(diethylamino)chlorophosphane, prepared as described by J. Sakai, W. B. Schweizer, D. Seebach in Helv. Chim. Acta 1993, 76, 2654-2665 (1.62 g, 7.7 mmol, 1 eq), was then added quickly. The reaction mixture was subsequently warmed to room temperature overnight. The solvent was taken off under reduced pressure, the residue was taken up in diethyl ether (30 ml) and admixed with degassed water (0.14 g, 0.14 ml, 7.8 mmol, 1 eq). The suspension formed was filtered through Celite and magnesium sulfate under a protective gas atmosphere. The solvent was removed at reduced pressure. The crude product was purified by means of bulb tube distillation at 200° C. (10$^{-3}$ mbar). The title compound was obtained as a viscous, colorless liquid (1.41 g, 4.0 mmol, 52%).

$^1$H-NMR (300.064 MHz, C$_6$D$_6$):

δ=1.05 (s, 9H, C(CH$_3$)$_3$), 1.10 (t, 12H, J=7.0 Hz, CH$_2$CH$_3$), 3.07 (m, 8H, CH$_2$CH$_3$), 7.25 (d, 2H, J=3.1 Hz, Ar—H), 8.01 (b, 1H, NH), 8.48 (dd, 1H, J=5.0 Hz, J=4.0 Hz, Ar—H).

$^{13}$C-NMR (100.620 MHz, C$_6$D$_6$):

δ=14.9 (s, 3C, C(CH$_3$)$_3$), 27.3 (s, 4C, CH$_2$CH$_3$), 39.6 (s, 1C, C(CH$_3$)$_3$), 43.9 (d, 4C, J$_{P,C}$=17.4 Hz, CH$_2$CH$_3$), 111.6 (d, 1C, J$_{P,C}$=2.9 Hz, Ar—CH), 122.8 (d, 1C, J$_{P,C}$=21.8 Hz, C5), 137.6 (s, 1C, Ar—CH), 152.4 (d, 1C, J$_{P,C}$=7.3 Hz, Ar—C), 164.8 (d, 1C, J$_{P,C}$=13.1 Hz, Ar—C), 176.1 (s, 1C, C=O).

$^{31}$P-NMR (121.468 MHz, C$_6$D$_6$):

δ=94.3(s)

b) Synthesis of 6-(3,5-dioxa-4-phosphacyclohepta[2,1-a; 3,4-a']dinaphthalen-4-yl)-2-pivaloylaminopyridine

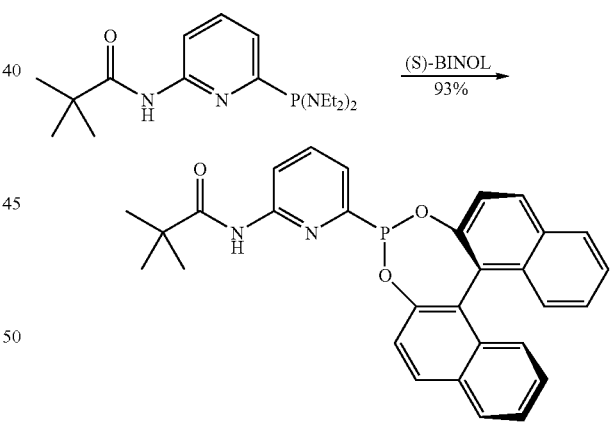

N-(6-(bis(diethylamino)phosphino)pyridin-2-yl)pivalamide (0.292 g, 0.60 mmol, 1 eq) was dissolved in toluene (12 ml). (S)-BINOL (0.172 g, 0.60 mmol, 1 eq) was subsequently added and the reaction mixture was refluxed for 3 hours. The solvent was removed under reduced pressure. The title compound could be obtained in the form of a white solid (0.276 g, 0.56 mmol, 93%).

$^1$H-NMR (300.064 MHz, CDCl$_3$):

δ=1.37 (s, 9H, C(CH$_3$)$_3$), 6.71 (d, 1H, J=8.8 Hz, Ar—H), 6.98 (d, 1H, J=7.5 Hz, Ar—H), 7.15-7.47 (m, 7H, Ar—H), 7.62 (pt, 2H, J=8.9 Hz, Ar—H), 7.83 (d, 1H, J=8.1 Hz,

Ar—H), 7.96 (d, 1H, J=8.0 Hz, Ar—H), 8.04 (d, 1H, J=8.8 Hz, Ar—H), 8.16 (b, 1H, NH), 8.27 (d, 1H, J=8.5 Hz, Ar—H).

$^{31}$P-NMR (121.468 MHz, CDCl$_3$):

δ=167.2 (s)

Example 5

Preparation of a Heterodimeric Pt Complex

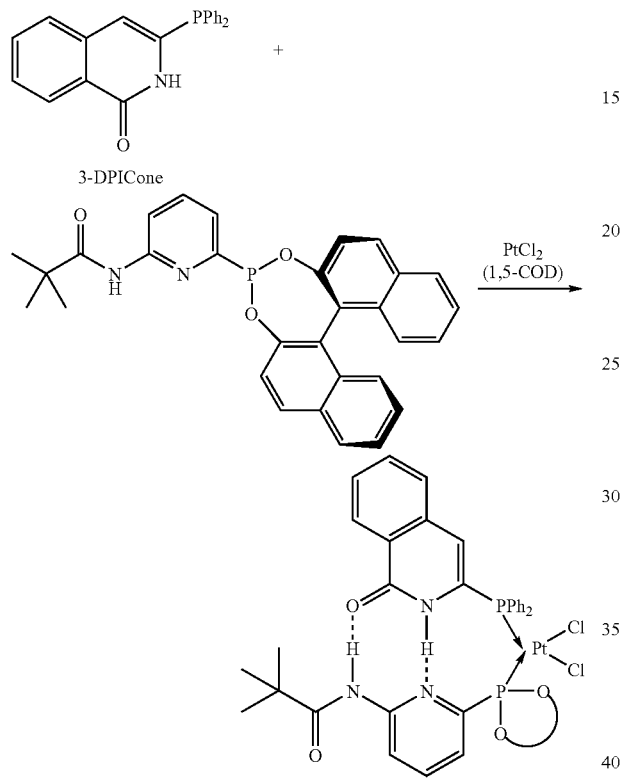

A solution of 3-DPICone (8.8 mg, 2.67×10$^{-2}$ mmol, 1 eq) and aminopyridine ligand (13.2 mg, 2.67×10$^{-2}$ mmol, 1 eq) in CDCl$_3$ (0.4 ml) was added to a solution of PtCl$_2$(1,5-cyclooctadiene) (10.0 mg, 2.67×10$^{-2}$ mmol, 1 eq) in CDCl$_3$ (0.4 ml). The formation of the heteroleptic complex was observed by means of NMR spectroscopy.

$^{31}$P-NMR (121.468 MHz, CDCl$_3$):

δ=17.2 (dd, $^{1}J_{P1-P}$=3590 Hz, $^{2}J_{P-P}$=13.4 Hz), 108.0 (d, $^{2}J_{P-P}$=13.4 Hz).

The invention claimed is:

1. A ligand selected from among compounds of the formulae I.i to I.iii

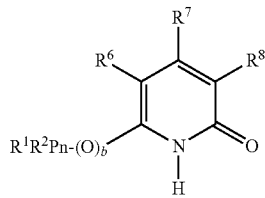
(I.i)

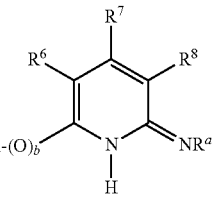
(I.ii)

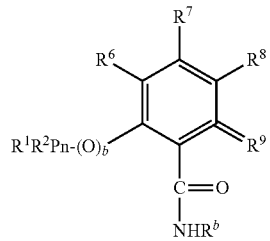
(I.iii)

and the tautomers thereof, where b is 0 or 1,

Pn is P, As or Sb, and

R1 and R2 are bridged so that they form a pnicogen-comprising group of the formula

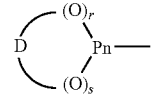

wherein r and s are independently of another 0 or 1,

D together with the phosphorus atom and the oxygen atom(s) to which it is bound forms a 4- to 8-membered heterocycle which may be fused with one, two or three cycloalkyl, heterocycloalkyl, aryl and/or hetaryl groups, where the fused-on groups may each independently of one another bear one, two, three or four substituents selected from among alkyl, alkoxy, halogen, sulfonate, NE4E5, alkylene-NE4E5, nitro, cyano and carboxylate, and/or D may bear one, two, three or four substituents selected from among alkyl, hydroxy, alkoxy, optionally substituted cycloalkyl and optionally substituted aryl, and/or D may be interrupted by 1, 2 or 3 optionally substituted heteroatoms, and $R^6$ to $R^9$ are each, independently of one another, hydrogen, $C_1$-$C_4$-alkyl, $C_1$-$C_4$-alkoxy, aryl, heteroaryl, acyl, halogen, $C_1$-$C_4$-alkoxycarbonyl or carboxylate, where two vicinal radicals $R^6$ to $R^9$ may also form a fused ring system, and $R^a$ and $R^b$ are each hydrogen, alkyl, cycloalkyl or aryl, and $R^a$ can also be acyl.

2. The ligand as claimed in claim 1, selected from among compounds of the formulaes

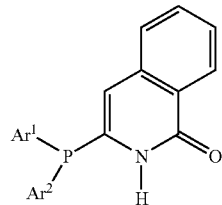

Ar¹, Ar²=phenyl, phenyl 1-naphthyl, 1-naphthyl phenyl, 1-naphthyl
if the ligand is of the formulae I.i

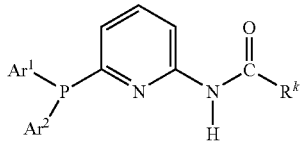

Ar¹, Ar²=Phenyl, Phenyl 1-Naphthyl, 1-Naphthyl Phenyl, 1-Naphthyl
$R^k$=Methyl, Ethyl, n-Propyl, Isopropyl, n-Butyl, tert-Butyl
if the ligand is of the formulae I.ii, and

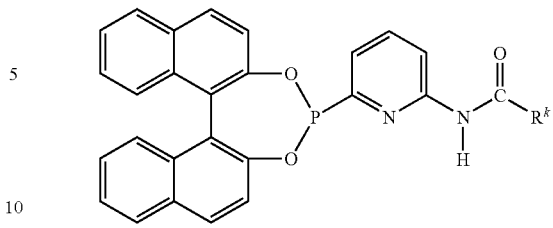

$R^k$=Methyl, Ethyl, n-Propyl, Isopropyl, n-Butyl, tert-Butyl
if the ligand is of the formulae I.iii.

3. A catalyst comprising a transition metal complex having ligands which each have a pnicogen-comprising or pseudopnicogen-comprising group and at least one functional group capable of forming intermolecular noncovalent bonds, the ligands being dimerized via intermolecular noncovalent bonds, and the ligands being selected from among the compounds of formulas I.i to I.iii, as defined in claim 1.

4. A catalyst comprising a transition metal complex having ligands which each have a pnicogen-comprising or pseudopnicogen-comprising group and at least one functional group capable of forcing intermolecular noncovalent bonds, the ligands being dimerized via intermolecular noncovalent bonds, and the ligands being selected from among the compounds of formulaes I.i to I.iii, as defined in claim 2.

* * * * *